(12) United States Patent
Wellinghoff et al.

(10) Patent No.: US 6,277,408 B1
(45) Date of Patent: Aug. 21, 2001

(54) SILICATE-CONTAINING POWDERS PROVIDING CONTROLLED, SUSTAINED GAS RELEASE

(75) Inventors: Stephen T. Wellinghoff, San Antonio; Joel J. Kampa, Boerne, both of TX (US); Sumner A. Barenberg, Chicago, IL (US); Peter N. Gray, Chicago, IL (US); Michael D. Lelah, Chicago, IL (US)

(73) Assignees: Southwest Research Institute, San Antonio, TX (US); Bernard Technologies, Inc., Chicago, IL (US)

( * ) Notice: Subject to any disclaimer, the term of this patent is extended or adjusted under 35 U.S.C. 154(b) by 0 days.

(21) Appl. No.: 09/383,001

(22) Filed: Aug. 25, 1999

Related U.S. Application Data
(60) Provisional application No. 60/074,003, filed on Feb. 9, 1998.

(51) Int. Cl.[7] .................................................. A61K 9/24
(52) U.S. Cl. ............................................................ 424/473
(58) Field of Search ............................................ 424/473

(56) References Cited

U.S. PATENT DOCUMENTS

| | | | |
|---|---|---|---|
| 2,071,625 | 2/1937 | Haas et al. .............................. 99/172 |
| 2,482,891 | 9/1949 | Aston .................... 252/187 |
| 2,546,568 | 3/1951 | Taylor .................... 99/150 |
| 2,558,942 | 7/1951 | Eagleson ................ 167/30 |
| 3,183,057 | 5/1965 | Marks et al. .............. 21/58 |
| 3,585,147 | 6/1971 | Gordon ................... 252/187 |
| 3,591,515 | 7/1971 | Lovely .................... 252/187 |
| 3,767,787 | 10/1973 | Segal ...................... 424/76 |
| 4,104,190 | 8/1978 | Hartshorn ................ 252/187 R |
| 4,330,531 | 5/1982 | Alliger ................... 424/149 |
| 4,499,077 | 2/1985 | Stockel et al. ........... 424/149 |
| 4,504,442 | 3/1985 | Rosenblatt et al. ..... 422/37 |
| 4,547,381 | 10/1985 | Mason et al. ........... 426/316 |
| 4,585,482 | 4/1986 | Tice et al. .............. 106/15.05 |
| 4,681,739 | 7/1987 | Rosenblatt et al. ..... 422/37 |
| 4,689,169 | 8/1987 | Mason et al. .......... 252/186.24 |
| 4,728,498 | 3/1988 | Theeuwes ............... 422/29 |
| 4,748,904 | 6/1988 | Razeto et al. ......... 99/467 |
| 4,829,129 | 5/1989 | Kelley ................... 525/326.9 |
| 4,880,638 | 11/1989 | Gordon .................. 424/662 |
| 4,889,654 | 12/1989 | Mason et al. ......... 252/100 |
| 4,891,216 | 1/1990 | Kross et al. ........... 424/78 |
| 4,925,645 | 5/1990 | Mason ................... 423/477 |
| 4,956,184 | 9/1990 | Kross ..................... 424/661 |
| 4,966,775 | 10/1990 | Donofrio et al. ...... 424/661 |
| 4,975,109 | 12/1990 | Friedman, Jr. et al. .. 71/67 |
| 4,986,990 | 1/1991 | Davidson et al. ...... 424/665 |
| 5,106,596 | 4/1992 | Clemes .................. 422/305 |
| 5,116,575 | 5/1992 | Badertscher et al. .. 422/28 |
| 5,126,070 | 6/1992 | Leifheit et al. ...... 252/186.36 |
| 5,252,343 | 10/1993 | Kross ..................... 424/661 |
| 5,306,440 | 4/1994 | Ripley et al. ......... 252/186.33 |
| 5,352,467 | 10/1994 | Mitchell et al. ...... 426/316 |
| 5,360,609 | 11/1994 | Wellinghoff ........... 514/772.3 |
| 5,384,134 | 1/1995 | Kross et al. ........... 424/661 |
| 5,387,350 | 2/1995 | Mason ................... 210/754 |
| 5,399,288 | 3/1995 | Marzouk et al. ..... 252/186.21 |
| 5,405,549 | 4/1995 | Pitochelli ............. 252/187.21 |
| 5,597,599 | 1/1997 | Smith et al. ........... 426/316 |
| 5,631,300 | 5/1997 | Wellinghoff ........... 514/772.3 |
| 5,639,295 | 6/1997 | Wellinghoff et al. .. 106/15.05 |
| 5,650,446 | 7/1997 | Wellinghoff et al. .. 514/772.3 |
| 5,668,185 | 9/1997 | Wellinghoff ........... 514/772.3 |
| 5,695,814 | 12/1997 | Wellinghoff et al. .. 427/213 |
| 5,705,092 | 1/1998 | Wellinghoff et al. .. 252/187.21 |
| 5,707,739 | 1/1998 | Wellinghoff et al. .. 428/403 |
| 5,719,100 | 2/1998 | Zahradnik et al. .... 502/417 |
| 5,888,528 | 3/1999 | Wellinghoff et al. .. 424/405 |
| 5,914,120 | 6/1999 | Wellinghoff et al. .. 424/406 |
| 5,922,776 | 7/1999 | Wellinghoff et al. .. 514/772.3 |
| 5,965,264 | 10/1999 | Barenberg et al. ... 428/402 |
| 5,980,826 | 11/1999 | Barenberg et al. ... 422/37 |

FOREIGN PATENT DOCUMENTS

| | | |
|---|---|---|
| 1 048 200 | 1/1991 | (CN) . |
| 0 287 074 | 4/1988 | (EP) . |
| 0 611 162 | 2/1994 | (EP) . |
| 0 611 163 | 2/1994 | (EP) . |
| 1208804 | 10/1978 | (GB) . |
| 2151138 | 12/1984 | (GB) . |
| 57-198775 | 12/1982 | (JP) . |
| 60-092759 | 5/1985 | (JP) . |
| 1119256 | 5/1989 | (JP) . |
| 4-164005 | 6/1992 | (JP) . |
| 6-107971 | 4/1994 | (JP) . |
| WO 85/04107 | 3/1985 | (WO) . |
| WO 88/09176 | 5/1988 | (WO) . |
| WO 96/18300 | 6/1996 | (WO) . |

*Primary Examiner*—Kevin E. Weddington
(74) *Attorney, Agent, or Firm*—Senniger, Powers, Leavitt & Roedel

(57) ABSTRACT

A particle including anions dispersed throughout an amorphous, paracrystalline or crystalline solid solution, the anions being capable of reacting with hydronium ions to generate a gas. The particle can be incorporated into a powder capable of generating and releasing a gas after hydrolysis of an acid releasing agent.

5 Claims, 10 Drawing Sheets

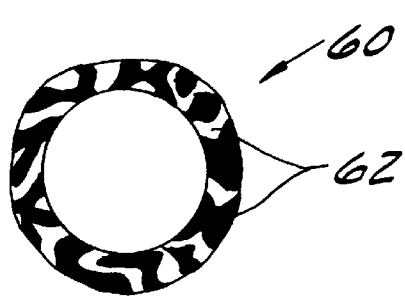
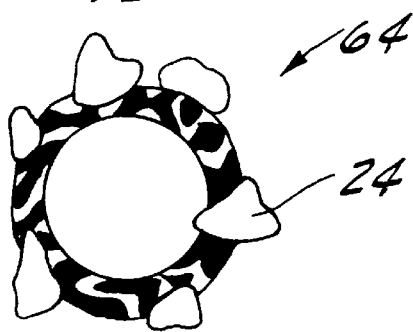
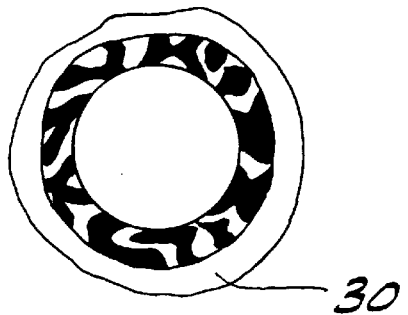
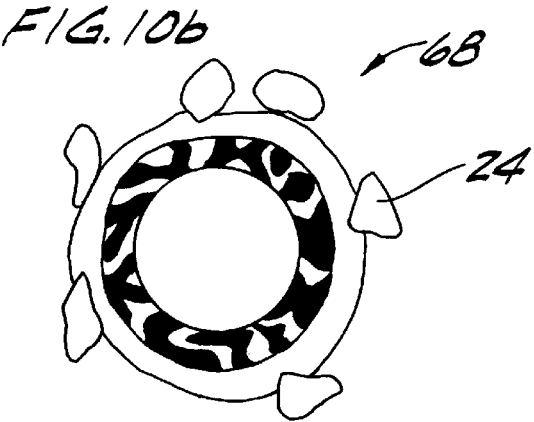

SILICATE-CONTAINING POWDERS PROVIDING CONTROLLED, SUSTAINED GAS RELEASE

REFERENCE TO RELATED APPLICATIONS

This application is a continuation-in-part application of provisional U.S. Ser. No. 60/074,003 filed Feb. 9, 1998.

BACKGROUND OF THE INVENTION

The present invention relates generally to a particle, a powder incorporating such particles for providing sustained release of a gas, and a product such as a film or coating which incorporates the powder for sustained gas release. The invention particularly relates to a silicate particle containing anions capable of reacting with a hydronium ion to generate a gas, and a powder containing such silicate particles for retarding, controlling, killing or preventing microbiological contamination (e.g., bacteria, fungi, viruses, mold spores, algae, and protozoa), deodorizing, enhancing freshness, and/or retarding, preventing or controlling chemotaxis by release of a gas or a combination of gases, such as chlorine dioxide, sulfur dioxide, nitrogen dioxide, nitric oxide, nitrous oxide, carbon dioxide, hydrogen sulfide, hydrocyanic acid, dichlorine monoxide, or chlorine.

Chlorine dioxide ($ClO_2$) is a superior oxidizing agent widely used as a bleach, disinfectant, fumigant or deodorizer. It can penetrate the cell wall or membrane and cytoplasm of mold spores, bacteria and other microbiological contaminants at concentrations below one part per million and destroy them.

The incorporation of chlorine dioxide or sodium chlorite in food packaging has prompted studies to determine whether residual levels of such preservatives result in a significant genetic or carcinogenic hazard to humans. Meier et al. studied the effect of subchronic and acute oral administration of chlorine, chlorine dioxide, sodium chlorite and sodium chlorate on the induction of chromosomal aberrations and spermhead abnormalities in mice [Environ. Mutagenesis, 7, 201 (1985)]. Only the highly reactive hypochlorite resulted in a weak positive effect for mutagenic potential. The other compounds, including chlorine dioxide and sodium chlorite, failed to induce any chromosomal aberrations or increased numbers of micronuclei in the bone marrow of mice. Vilagines et al. attribute the relatively innocuous effect of chlorine dioxide to its inability to produce halomethanes, unlike hypochlorite and chlorine [Proc. AWWA Disinfect. Semin., 24 pp. (1977); Chem. Abs. 93, 173513f]. Recently, Richardson et al. reported that an extensive study of the reaction of chlorine dioxide with water borne organics by the Environmental Protection Agency confirmed this observation [Environ. Sci. Technol., 28, 592 (1994)].

Japanese Kokai Nos. 63/296,758, 63/274,434, and 57/168,977 describe deodorants containing chlorine dioxide incorporated in a polymer, ceramic beads, or calcium silicate wrapped in nonwoven cloth, respectively. Gels that generate chlorine dioxide for use as topical applications for disinfection are disclosed by Kenyon et al., Am. J. Vet. Res., 45(5), 1101 (1986). Chlorine dioxide generating gels are generally formed by mixing a gel containing suspended sodium chlorite with a gel containing lactic acid immediately prior to use to avoid premature chlorine dioxide release. Chlorine dioxide releasing gels have also been used in food preservation.

Encapsulation processes have also been used in preparing sources of chlorine dioxide. Canadian Patent No. 959,238 describes generation of chlorine dioxide by separately encapsulating sodium chlorite and lactic acid in polyvinyl alcohol and mixing the capsules with water to produce chlorine dioxide.

Tice et al., U.S. Pat. No. 4,585,482 describe gradual hydrolysis of alternating poly(vinyl methyl ether-maleic anhydride) or poly(lactic-glycolic acid) to generate acid that can release chlorine dioxide from sodium chlorite. A polyalcohol humectant and water are encapsulated with the polyanhydride or polyacid in a nylon coating. After sodium chlorite is diffused into the capsule through the nylon wall, an impermeable polystyrene layer is coacervated around the nylon capsule. Solvents are required for reaction and application of the capsules. The capsules can be coated onto surfaces to release chlorine dioxide. Although the capsules are said to provide biocidal action for several days to months, chlorine dioxide release begins immediately after the capsules are prepared. The batchwise process used to prepare the capsules also involves numerous chemical reactions and physical processes, some of which involve environmental disposal problems.

Powders that release chlorine dioxide as soon as they are prepared have been formed by mixing acid solids and chlorite solids. Lovely, U.S. Pat. No. 3,591,515 describes a chlorite-containing powder that releases chlorine dioxide upon being admixed with an acid-containing powder. Hartshorn, U.S. Pat. No. 4,104,190 describes solid mixtures of sodium chlorite and citric, adipic or malic acid that are compressed to form tablets. Mason et al., U.S. Pat. Nos. 4,547,381 and 4,689,169 disclose mixtures of powdered sodium chlorite, acid and inert diluent that release chlorine dioxide without exposing the mixtures to ambient moisture. Tice et al., U.S. Pat. No. 4,585,482 describe solid admixtures of sodium chlorite and polylactic acid.

Klatte et al., U.S. Pat. Nos. 5,567,405 and 5,573,743, describe zeolite crystals impregnated with sodium chlorite, an acid, sodium sulfite, or sodium bisulfite by immersing the zeolite in an aqueous solution to adsorb anions onto its surface. Chlorine dioxide is said to be generated by passing a fluid containing oxygen through a bed containing a mixture of chlorite-impregnated zeolites and acid-impregnated zeolites.

Wellinghoff et al. have formulated composites that include a hydrophobic phase containing an acid releasing agent and a hydrophilic phase containing chlorite anions. The composite is substantially free of water and gas (e.g., chlorine dioxide) until it is exposed to moisture. Once exposed to moisture, acid and hydronium ions are generated in the hydrophobic phase. The hydronium ions migrate to the hydrophilic phase and react with chlorite anions to generate chlorine dioxide from the composite. The composite can be in the form of a powder including a hydrophobic core containing an acid releasing agent, and particles containing chlorite anions on a surface of the core. These composites are composed of and generate only substances used in foods or substances generally recognized as safe or inert substances. The composites can be used for food packaging and other applications where the substances can be ingested by or in contact with humans. These composites are described in U.S. Pat. Nos. 5,360,609, 5,631,300, 5,650, 446, 5,668,185, 5,695,814, 5,705,092, and 5,707,739. Such composites releasing gases such as sulfur dioxide, nitrogen dioxide, nitric oxide, nitrous oxide, carbon dioxide, hydrogen sulfide, hydrocyanic acid, dichlorine monoxide, or chlorine are described in Wellinghoff et al., U.S. Pat. No. 6,046,243.

Wellinghoff et al. U.S. Pat. No. 5,914,120 discloses a composite formulated for maximum chlorine dioxide release in which the hydrophilic material contains an α-amino ether, ester or alcohol and a chlorite salt formed by reaction of an iminium chlorite and a base. Iminium chlorite is unstable to nucleophilic attack by the chlorite anion. When the iminium chlorite is reacted with a base, however, the more stable α-amino ether, ester or alcohol and a chlorite salt are formed.

Wellinghoff et al. U.S. Pat. No. 5,639,295 describes a method for maximizing chlorine dioxide release from an amine-containing composite by omitting the chlorite source until the composite is applied to a surface. After application, the composite is exposed to chlorine dioxide gas that either reacts with the amine to form iminium chlorite in situ or reacts with the amine to provide chlorite anions. The composite is then activated in the presence of moisture to release chlorine dioxide. The composite can be exposed to elevated temperatures during processing, storage and application before reaction to form iminium chlorite because the hydrophilic material does not contain iminium chlorite or any chlorite anions that could decompose at such temperatures. The method also precludes premature release of chlorine dioxide from the composite.

Barenberg et al. U.S. Pat. No. 5,980,826 and Wellinghoff et al. U.S. Pat. No. 6,046,243 describe numerous methods of using composites such as those disclosed by Wellinghoff et al. to retard bacterial, fungal, and viral contamination and growth of molds on food, produce, meat, and other materials and to deodorize materials such as textiles and storage spaces.

Wellinghoff et al. U.S. Pat. No. 5,922,776 describes transparent compositions that provide sustained release of chlorine dioxide.

Wellinghoff et al. U.S. Pat. No. 5,888,528 discloses powders containing a hydrophilic core, a hydrophobic layer on an outer surface of the hydrophilic core, and particles in contact with the hydrophobic layer. The hydrophobic layer contains an acid releasing agent. The particles contain an anhydrous material capable of binding with water. The core, the particles, and the hydrophobic layer are substantially free of water, and the core is capable of generating and releasing a gas after hydrolysis of the acid releasing agent.

There is a need for an inert powder that can be easily activated to initiate release of chlorine dioxide or another biocidal or deodorizing gas in use. A powder that, except for the anions therein for generating the biocidal gas, is composed of and reacts to provide residues composed of only substances usable in foods, or those generally recognized as safe or inert substances, is particularly needed for food packaging, modified atmosphere packaging, and other applications where the substances can be ingested by or in contact with humans. Although the Wellinghoff et al. composites are effective biocides, there is a need for biocidal compositions that can be more readily manufactured and provide more control or flexibility for sustained release of a gas.

SUMMARY OF THE INVENTION

Among the objects of the invention, therefore, may be noted the provision of a powder or percolation network that releases a concentration of chlorine dioxide or other biocidal gas sufficient to eliminate bacteria, fungi, molds, algae, protozoa and viruses; the provision of a powder or percolation network that releases a concentration of a gas that retards, prevents or controls biochemical decomposition, controls respiration, retards, prevents or controls chemotaxis, enhances freshness or deodorizes; the provision of such a powder or percolation network that releases such gas concentrations after activation for a period of up to several months; the provision of such a powder or percolation network that begins to release a gas under controlled or sustained conditions within minutes, hours, days, weeks or months after being activated by moisture; the provision of such a powder or percolation network having greater gas release efficiency compared to known compositions; the provision of such a powder that is free-flowing and can be easily blended with other ingredients prior to application; the provision of such a powder that can penetrate porous surfaces; the provision of such a powder or percolation network that increases the release rate of chlorine dioxide or other gas in response to increased levels of temperature and humidity, which promote mold and bacteria growth, so that the gas release does not start until a critical humidity is achieved whose value is determined by the structure of the powder; the provision of such a powder or percolation network that, except for the anions therein for generating the biocidal gas, only contains substances approved for human exposure; the provision of such a powder or percolation network that is odorless; the provision of a process for preparing a powder which requires few reactions or physical processes to provide sustained release of chlorine dioxide or other biocidal gases; the provision of such a process which allows for high temperature processing and application of the powder without thermal decomposition thereof; the provision of such a process which utilizes relatively inexpensive starting materials to minimize applications cost; and the provision of such a process which reduces manufacturing hazards and disposal requirements as compared to most conventional processes for preparing chlorine dioxide releasing powders.

The present invention is directed to a particle containing anions dissolved in an amorphous, paracrystalline or crystalline solid solution. The anions are capable of reacting with hydronium ions to generate a gas.

The particles are prepared by a process including the steps of admixing an amorphous, paracrystalline or crystalline material, a solvent, and a chlorite, bisulfite, sulfite, hydrosulfide, nitrite, hypochlorite, or cyanide salt to form a solution and forming the particles containing an amorphous, paracrystalline or crystalline solid solution from the solution.

The invention is also directed to a silicate particle containing anions dispersed throughout substantially amorphous silicate. The anions are capable of reacting with hydronium ions to generate a gas.

The silicate particles are prepared by a process including the steps of admixing a silicate, a solvent, and a chlorite, bisulfite, sulfite, hydrosulfide, nitrite, hypochlorite, or cyanide salt to form a solution, and forming substantially amorphous silicate particles from the solution.

The present invention is also directed to a powder for sustained release of a gas, wherein the powder includes anions dissolved in an amorphous, paracrystalline or crystalline solid solution, and an acid releasing agent. The anions are capable of reacting with hydronium ions to generate a gas. The powder is substantially free of water and capable of generating and releasing a gas after hydrolysis of the acid releasing agent.

Another embodiment of the invention is directed to a powder for sustained release of a gas, wherein the powder contains an interpenetrating network. The interpenetrating network contains a silicate, anions that are capable of reacting with hydronium ions to generate a gas, and an acid releasing agent. The powder is substantially free of water and capable of generating and releasing a gas after hydrolysis of the acid releasing agent.

Another embodiment of the invention is directed to a powder for sustained release of a gas, wherein the powder includes a core containing a silicate and anions that are capable of reacting with hydronium ions to generate a gas, a first layer containing an acid releasing agent, and a second layer between the core and the first layer. The second layer contains a silicate. The core and the first and second layers are substantially free of water. The second layer is substantially water-insoluble, and the core is capable of generating and releasing a gas after hydrolysis of the acid releasing agent.

The present invention is also directed to a powder for sustained release of a gas, wherein the powder includes a core containing a silicate and anions that are capable of reacting with hydronium ions to generate a gas, and a layer on the outer surface of the core. The layer contains an acid releasing agent and a silicate. The core and the layer are substantially free of water, the layer is substantially water-insoluble, and the core is capable of generating and releasing a gas after hydrolysis of the acid releasing agent.

Another aspect of the invention is directed to a composition comprising a hydrophobic phase and a hydrophilic phase containing a percolation agent and a gas-generating agent, such as any of the powders described above. The composition is a co-continuous network or a discontinuous network which contains passages formed by the percolation agent. The passages are capable of transmitting moisture to the gas-generating material to generate and release a gas.

The powders are prepared by admixing particles containing a silicate and anions that are capable of reacting with hydronium ions to generate a gas with a solvent to form a slurry, admixing a zinc, magnesium, calcium, aluminum or other monovalent, divalent or multivalent salt and an acid releasing agent with the slurry to form a solids-containing suspension, and forming a powder from the solids-containing suspension. The powder is substantially free of water and capable of generating and releasing the gas after hydrolysis of the acid releasing agent.

Another process for preparing powders of the invention includes the steps of admixing a zinc, magnesium, calcium, aluminum or other monovalent, divalent or multivalent salt, an acid releasing agent, and particles containing a silicate and anions that are capable of reacting with hydronium ions to generate a gas with a solvent to form a solids-containing suspension, and forming a powder from the solids-containing suspension. The powder is substantially free of water and capable of generating and releasing a gas after hydrolysis of the acid releasing agent.

Another process for preparing powders of the invention includes the steps of admixing a silicate, a solvent, an acid releasing agent, and a chlorite, bisulfite, sulfite, bicarbonate, carbonate, hydrosulfide, nitrite, hypochlorite, or cyanide salt to form a solution, and forming a powder from the solution. The powder is substantially free of water and capable of generating and releasing a gas after hydrolysis of the acid releasing agent.

Another embodiment of the invention is a process for preparing a composition providing sustained release of a gas by admixing a percolation agent and a gas-generating material to form a powdered mixture, admixing the powdered mixture with a hydrophobic material to form a blend, heating the blend to form a melt, and cooling the melt to form the composition. The composition is a co-continuous network or a discontinuous network which contains passages formed by the percolation agent. The passages are capable of transmitting moisture to the gas-generating material to generate and release a gas.

Yet another embodiment of the invention is directed to a process for preparing a composition providing sustained release of a gas by admixing a percolation agent and a gas-generating material to form a powdered mixture, admixing the powdered mixture with a melted hydrophobic material to form a melt, and cooling the melt to form the composition. The composition is a co-continuous network or a discontinuous network which contains passages formed by the percolation agent. The passages are capable of transmitting moisture to the gas-generating material to generate and release a gas.

Another embodiment of the invention is directed to a method of retarding, killing, preventing or controlling microbiological contamination on a surface of a material, within the material or in the atmosphere surrounding the material, by exposing a surface of a material to the powder, and exposing the surface to moisture to generate and release a biocidal gas from the powder into the atmosphere surrounding the surface.

The invention is also directed to a method of retarding, killing, preventing or controlling microbiological contamination on a surface of a material, within the material or in the atmosphere surrounding the material, by placing a material adjacent the powder, and exposing the powder to moisture to release a biocidal gas from the powder into the atmosphere surrounding the material.

The invention is also directed to a method of retarding, preventing or controlling biochemical decomposition on a surface of a material or within the material by exposing a surface of a material to a powder of the invention, and exposing the surface to moisture to generate and release a biochemical decomposition-inhibiting gas from the powder into the atmosphere surrounding the surface.

Another embodiment of the invention is directed to a method of retarding, preventing or controlling biochemical decomposition on a surface of a material or within the material by placing the material adjacent a powder of the invention, and exposing the powder to moisture to release a biochemical decomposition-inhibiting gas from the powder into the atmosphere surrounding the material.

Yet another embodiment of the invention is a method of controlling respiration of a material by exposing a surface of a material to a powder of the invention, and exposing the surface to moisture to generate and release a respiration-controlling gas from the powder into the atmosphere surrounding the surface.

Another embodiment of the invention is a method of controlling respiration of a material by placing the material adjacent a powder of the invention, and exposing the powder to moisture to release a respiration-controlling gas from the powder into the atmosphere surrounding the material.

The invention is also directed to a method of deodorizing a surface of a material or the atmosphere surrounding the material or enhancing freshness of the material, by exposing a surface of a material to the powder, and exposing the surface to moisture to generate and release a deodorizing gas from the powder into the atmosphere surrounding the surface.

Yet another embodiment of the invention is directed to a method of deodorizing a surface of a material or the atmosphere surrounding the material or enhancing freshness of the material, by placing a material adjacent the powder, and exposing the powder to moisture to release a deodorizing gas from the powder into the atmosphere surrounding the material.

Another embodiment of the invention is directed to a method of retarding, preventing or controlling chemotactic attraction of an organism to a material, by exposing a surface of a material to the powder, and exposing the surface to moisture to generate and release an odor-masking or odor-neutralizing gas from the powder into the atmosphere surrounding the surface.

The invention is also directed to a method of retarding, preventing or controlling chemotactic attraction of an organism to a material, by placing a material adjacent the powder, and exposing the powder to moisture to release an odor-masking or odor-neutralizing gas from the powder into the atmosphere surrounding the material.

Other objects and advantages of the invention will be apparent from the following detailed description.

BRIEF DESCRIPTION OF THE DRAWINGS

FIGS. 1a–10b are schematics of particles for providing sustained release of a gas;

DETAILED DESCRIPTION OF THE PREFERRED EMBODIMENTS

Figure 1A:
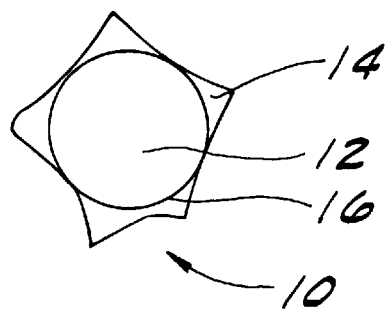

In accordance with the present invention, it has been discovered that anions such as chlorite which are used to generate a gas can be stabilized against thermal decomposition by dispersing the anions in a particle containing an amorphous, paracrystalline or crystalline solid solution via a spray drying process. When the particle is dried to a moisture level of up to about 10 wt. %, the particle dissolves very slowly in water which allows for processing of the particles to make powders for sustained release of a gas.

It has also been discovered that various powders prepared by admixing the particle with an acid releasing agent provide sustained release of a gas after being exposed to moisture. Although anions such as chlorite, bisulfite and bicarbonate can decompose at typical processing temperatures, the powders of the invention are thermally stable because the anions are stabilized within the solid solution, such as a silicate matrix. In a preferred embodiment, the powder includes anions uniformly dispersed and encapsulated within a substantially amorphous silicate matrix that is encapsulated by a substantially insoluble silicate layer which separates the matrix from an acid releasing layer. In another embodiment, the powder includes a substantially amorphous interpenetrating network containing anions, a substantially insoluble silicate, and the acid releasing agent. Since the thermal decomposition temperature of the anions is increased when incorporated in the powder, the powder can be processed at relatively high temperatures as compared to processing the anions per se and provides sustained release of a gas. Release of gas from the powder is optionally controlled by surrounding the powder with a hydrophobic material, a dispersant, anhydrous particles, a water-soluble material, a water-degradable material or a water-swellable material to control and delay release of gas from the powder for minutes to months after activation by moisture. The powder is easily prepared and can be used as is or incorporated into various end-use products, such as films, adhesives, granular blends, powdered compositions and formed objects such as tablets. The powder can also be composed entirely of inorganic materials so that it is odorless.

Particles of the Invention

In one embodiment of the invention, a particle is comprised of anions dissolved within an amorphous, paracrystalline or crystalline solid solution. The anions are capable of reacting with hydronium ions to generate a gas. The particle contains one or more phases, which may be amorphous, paracrystalline or crystalline, with the anions dissolved in one or more of the phases. In these phases, the dissolved anions are either randomly distributed (e.g., a solid solution), or distributed in an ordered crystalline lattice in which the anions are substantially prevented from being neighbors. The anions can be an interstitial component of an alloy or other crystalline solid solution, or can be dissolved in a glass or other amorphous or paracrystalline solid solution. A paracrystalline solid solution is generally a material having one or more phases that exhibit some characteristics of a crystalline state as demonstrated, for example, by broadening of the reflections in the x-ray diffraction pattern. The amorphous, paracrystalline or crystalline material is not a zeolite or other material which must be heated at a temperature that would destroy the anions in order to dissolve the anions in the material. Preferably, the particle is comprised of a substantially amorphous silicate. For purposes of the present invention, the term "substantially amorphous" is defined as including no more than 20% crystalline inclusions, preferably no more than 10%, and more preferably no more than 2%.

The silicate particle is preferably in the form of a substantially amorphous silicate matrix in which the anions are uniformly dispersed and encapsulated. The silicate particles generally range in size between about 0.1 and about 1,000 microns depending upon the intended end use, and can be made of any size possible via any solid forming process, but preferably via spray drying. The silicate particles are either solid or hollow, and are generally substantially spherical.

In one embodiment of the invention, the particle includes an inert core which may be used, for example, to increase the density and size of the particle, change or control the generation and release characteristics of the particle, or change or control the humidity at which the particle is activated to begin gas release. The solid solution is applied to the inert core and forms a layer on an outer surface thereof. The inert core can be any porous or nonporous particle that is insoluble in water or an aqueous solution of a water miscible organic material, such as a clay, ceramic, metal, polymer or zeolite material.

A problem recognized in the art is disproportionation of chlorite in chlorite-containing crystalline particles to chlorate and chloride when exposed to temperatures above about 90° C. The formation of the chlorate and chloride anions reduces the amount of chlorine dioxide that can be generated by a powder containing the particles because these anions do not generate chlorine dioxide efficiently in the presence of an acid or hydronium ions. Such disproportionation is minimized with the silicate particles of the invention. The silicate particles can be processed at temperatures up to 220° C. for a period of time without significantly reducing the amount of gas that can be generated from a powder containing the particles. Without being bound by a particular theory of the invention, it is believed that the anions that are capable of reacting with hydronium ions to form a gas are dispersed within an amorphous silicate matrix which encapsulates the anions. Disproportionation of chlorite is avoided because intermolecular interactions between the chlorite anions are minimized in the amorphous silicate matrix. Such chlorite-containing silicate particles thermally decompose at a temperature above the decomposition temperature of sodium chlorite, enabling high temperature processing of the particles or powders containing the particles.

Preferably, each silicate particle comprises between about 3 wt. % and about 95 wt. % silicate, between about 1 wt. % and about 30 wt. % anions capable of reacting to generate a gas, and up to about 95 wt. % inert core. More preferably, the silicate particle comprises between about 4 wt. % and about 95 wt. % silicate, between about 1 wt. % and about 15 wt. % anions capable of reacting to generate a gas, and up to about 95 wt. % inert core.

The silicate particle is substantially free of water to minimize diffusion of the anions into solution when further processing the particle, such as when the particles are added to an aqueous slurry containing an acid releasing agent to form a powder for sustained release of a gas. For purposes of the present invention, the silicate particle is substantially free of water if the amount of water in the silicate particle does not provide a pathway for transmission of anions from the particle into a solvent. Preferably, each of the silicate particles includes up to about 10 wt. %, preferably up to about 5 wt. % water without providing such a pathway for diffusion from the particle to the solvent.

Any silicate that is soluble in water or a water solution of a water miscible organic material, such as an alcohol, acetone or dimethylformamide, can be used in the silicate particles of the invention. Suitable silicates include sodium silicate, sodium metasilicate, sodium sesquisilicate, sodium orthosilicate, borosilicates, and aluminosilicates. The ratio of silicon measured as $SiO_2$ to alkali metal cation measured as $M_2O$ in the silicate particles, wherein M is selected from the group consisting of sodium and potassium, is between about 2.5 and about 3.5, preferably between about 3.0 and about 3.5, most preferably about 3.2. Commercially available silicates suitable for use can contain additional salts and additives such as copper compounds.

The silicate particles also contain anions which react with hydronium ions to form a gas. The anions are generally provided by salts of the anions and a counterion. Suitable salts include an alkali metal chlorite, an alkaline-earth metal chlorite, a chlorite salt of a transition metal ion, a protonated primary, secondary or tertiary amine, or a quaternary amine, an alkali metal bisulfite, an alkaline-earth metal bisulfite, a bisulfite salt of a transition metal ion, a protonated primary, secondary or tertiary amine, or a quaternary amine, an alkali metal sulfite, an alkaline-earth metal sulfite, a sulfite salt of a transition metal ion, a protonated primary, secondary or tertiary amine, or a quaternary amine, an alkali metal sulfide, an alkaline-earth metal sulfide, a sulfide salt of a transition metal ion, a protonated primary, secondary or tertiary amine, or a quaternary amine, an alkali metal bicarbonate, an alkaline-earth metal bicarbonate, a bicarbonate salt of a transition metal ion, a protonated primary, secondary or tertiary amine, or a quaternary amine, an alkali metal carbonate, an alkaline-earth metal carbonate, a carbonate salt of a transition metal ion, a protonated primary, secondary or tertiary amine, or a quaternary amine, an alkali metal hydrosulfide, an alkaline-earth metal hydrosulfide, a hydrosulfide salt of a transition metal ion, a protonated primary, secondary or tertiary amine, or a quaternary amine, an alkali metal nitrite, an alkaline-earth metal nitrite, a nitrite salt of a transition metal ion, a protonated primary, secondary or tertiary amine, or a quaternary amine, an alkali metal hypochlorite, an alkaline-earth metal hypochlorite, a hypochlorite salt of a transition metal ion, a protonated primary, secondary or tertiary amine, or a quaternary amine, an alkali metal cyanide, an alkaline-earth metal cyanide, or a cyanide salt of a transition metal ion, a protonated primary, secondary or tertiary amine, or a quaternary amine. Preferred salts include sodium, potassium, calcium, lithium or ammonium salts of a chlorite, bisulfite, sulfite, sulfide, hydrosulfide, bicarbonate, carbonate, hypochlorite, nitrite, or cyanide. Commercially available forms of chlorite and other salts suitable for use, such as Textone (Vulcan Corp.), can contain additional salts and additives such as tin compounds to catalyze conversion to a gas.

The silicate particles optionally contain a base or a filler. The base controls release of gas from the particle by reacting with hydronium ions that diffuse into the particle from an acid releasing layer or interdiffuse into the anion-rich areas of the particle to form a salt. When the base is depleted, excess hydronium ions then react with the anions within the particle to form a gas. The filler controls release of a gas by creating a barrier to diffusion of hydronium ions. The amount of base or filler within the core can be adjusted to alter the time period before gas is released from the particle. For example, the concentration of the base or filler can be increased if a longer delay of gas release is desired. The silicate particle preferably includes a base or filler if chlorite anions are present in the particle to stabilize the chlorite during preparation of the particle or a powder containing the particle.

Any base that reacts with a hydronium ion or any filler can be incorporated in the silicate particle. Suitable bases or fillers include, but are not limited to, an alkali metal bicarbonate such as lithium, sodium, or potassium bicarbonate, an alkali metal carbonate such as lithium, sodium or potassium carbonate, an alkaline-earth metal bicarbonate, an alkaline-earth metal carbonate such as magnesium or calcium carbonate, a bicarbonate salt of a transition metal ion, a protonated primary, secondary or tertiary amine, or a quaternary amine such as ammonium bicarbonate, a carbonate salt of a transition metal ion, a protonated primary, secondary or tertiary amine, or a quaternary amine, an alkali metal hydroxide such as lithium, sodium or potassium hydroxide, an alkaline-earth metal hydroxide such as calcium or magnesium hydroxide, a hydroxide salt of a transition metal ion, a protonated primary, secondary or tertiary amine, or a quaternary amine such as ammonium hydroxide, an alkali metal phosphate such as dibasic or tribasic phosphate salts, an alkaline-earth metal phosphate such as bicalcium or tricalcium phosphate, a phosphate salt of a transition metal ion, a protonated primary, secondary or tertiary amine, or a quaternary amine, an alkali metal sulfate such as sodium or potassium sulfate, an alkaline-earth metal sulfate such as calcium or magnesium sulfate, a sulfate salt of a transition metal ion, a protonated primary, secondary or tertiary amine, or a quaternary amine such as ammonium sulfate, an alkali metal sulfonate such as sodium sulfonate, an alkaline-earth metal sulfonate, or a sulfonate salt of a transition metal ion, a protonated primary, secondary or tertiary amine, or a quaternary amine, an alkali metal borate such as borax, an alkaline-earth metal borate such as magnesium orthoborate, or a borate salt of a transition metal ion, a protonated primary, secondary or tertiary amine, or a quaternary amine.

Powders of the Invention Various powders incorporating the particle can be prepared according to the invention. Powders including coated particles are illustrated in FIGS. 1a–8b. These powders include a particle core surrounded by an acid releasing layer and, optionally, coatings or anhydrous particles that can delay or control generation and release of a gas. A powder including a particle as part of an interpenetrating network is shown in FIGS. 9a–10b. These powders include an interpenetrating network containing a silicate, anions and an acid releasing agent and, optionally, coatings or anhydrous particles that can delay generation and release of a gas. A powder comprised of a single phase solid solution or interpenetrating network can also be prepared without incorporating the particles.

Powders of Coated Silicate Particles

In one embodiment of the invention as shown in FIG. 1a, a powder is comprised of a plurality of particles 10 including a core 12 having an acid releasing layer 14 on an outer surface 16 of the core. The core 12 comprises a particle as described above. The layer 14 includes a silicate and an acid releasing agent. Preferably, the core contains a substantially amorphous silicate, and the silicate in the layer 14 is substantially water-insoluble. Although the layer 14 is preferably continuous and substantially uniform, a particle 10 having a discontinuous layer 14 of variable thickness provides acceptable, sustained release of a gas.

Figure 2A:
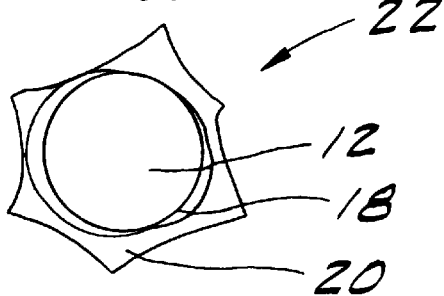

FIG. 2a illustrates a more preferred embodiment of the invention wherein a layer 18 containing a substantially water-insoluble silicate is between the core 12 and an acid releasing layer 20, forming a particle 22. The layer 18 minimizes diffusion of the anions into the solution used to prepare the powder, to minimize loss of anions needed to generate a gas. The layer 20 contains an acid releasing agent. Although the layers 18 and 20 are preferably continuous and substantially uniform, a particle 22 having discontinuous layers 18 and 20 of variable thickness provides acceptable, sustained release of a gas.

Figure 1B:
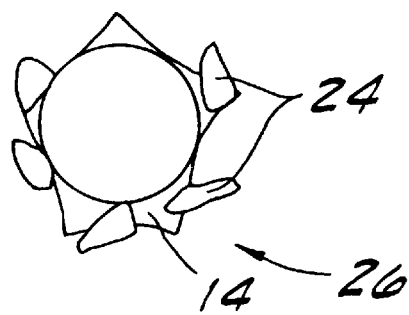
Figure 2B:
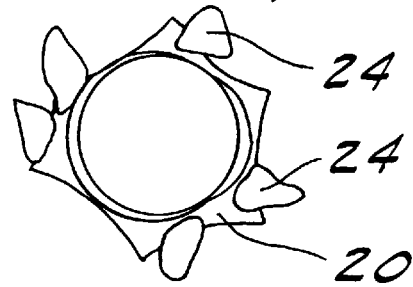

The particles 10 and 22 can also include particles 24 which contact the layer 14 or 20 as shown in FIGS. 1b and 2b to form particles 26 and 28, respectively. The particles 24 contain an anhydrous material capable of binding with water. For purposes of the present invention, an anhydrous material does not contain water, such as adsorbed water or water of crystallization.

When a powder 10, 20, 26 or 28 is exposed to ambient moisture or otherwise contacted with water, the water diffuses into the acid releasing layer 14 or 20. If the powder includes particles 24, the water binds to the particles 24 on the outer surface of the powder before diffusing into the layer 14 or 20. The acid releasing agent within the layer 14 or 20 is either an acid, a substance that can be hydrolyzed to an acid (i.e., a substance that reacts with the water that diffuses into the layer 14 or 20 to form an acid), or a mixture thereof. In either case, the acid in the layer 14 or 20 dissolves in the water that diffuses into the layer, forming hydronium ions and a counterion. The reaction products of this hydrolysis reaction are hydronium ions and counterions when the reaction proceeds to completion, or hydronium ions, counterions, acid and water when the reaction is in equilibrium. In FIGS. 2a and 2b, the hydronium ions resulting from the acid hydrolysis diffuse from the layer 20 into the layer 18. The hydronium ions diffuse from the layer 14 or 18 into the core 12, where they react with anions to generate a gas. The gas diffuses out of the powder into the surrounding atmosphere for a period of up to about six months to affect materials situated near the powder. Powders that release at least about $1.0 \times 10^{-6}$ gram gas/cm$^3$ for a period of at least one day, one week, one month or six months can be formulated by the processes of the present invention for a variety of end uses, including deodorization, freshness enhancement, chemotaxis control, delay or prevention such as reduction of insect infestation, biochemical decomposition control, reduction or prevention, respiration control, and control, delay, destruction or prevention of the growth of microorganisms such as bacteria, molds, fungi, algae, protozoa, and viruses on materials. Although the powders generally provide sustained release of a gas, the powders can be formulated so that gas is released during less than one day if desired for a particular end use.

Figure 3A:
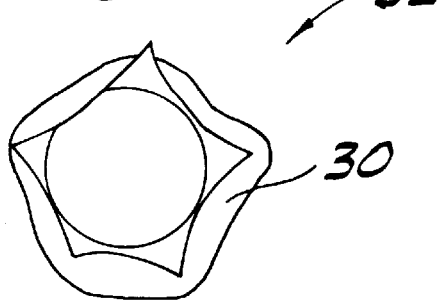

The powders of the invention can also be prepared to further delay generation of the gas as illustrated in FIGS. 3a–8b. In FIG. 3a, the particle 10 as shown in FIG. 1a is surrounded by a layer 30 containing a hydrophobic, water-soluble, water-degradable or water-swellable material to form a particle 32. In FIG. 4a, the particle 22 of FIG. 2a is surrounded by a layer 30 containing a hydrophobic, water-soluble, water-degradable or water-swellable material to form a particle 34. When the particle 32 or 34 coated with a water-soluble or water-degradable material is exposed to moisture, the water dissolves or degrades the material for a period of up to six months, preferably from several hours to one month, before water contacts the acid releasing agent. When the particle 32 or 34 coated with a water-swellable material is exposed to moisture, the water diffuses into the material and causes the material to expand for a period of up to six months, preferably from several hours to one month, before water contacts the acid releasing agent. Coating the particles 10 or 22 with a hydrophobic material also prolongs the diffusion of water into the acid releasing layer for a period of up to six months, preferably from several hours to one month. Gas release does not occur until enough moisture is transmitted by the hydrophobic layer 30 to provide a pathway for interdiffusion between the layers 14 or 20 and 30. After the water enters the acid releasing layer, gas release occurs according to the mechanism described above. Although the layers 14, 18, 20 and 30 are preferably continuous and substantially uniform, a particle 32 or 34 having discontinuous layers 14, 18, 20 or 30 of variable thickness provides acceptable, sustained release of a gas.

Figure 3B:
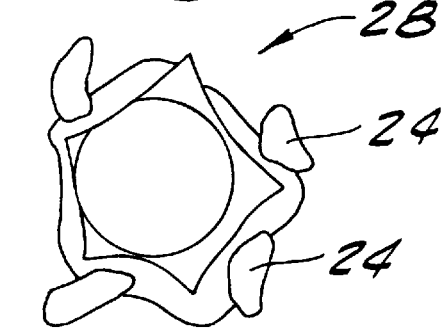
Figure 4A:
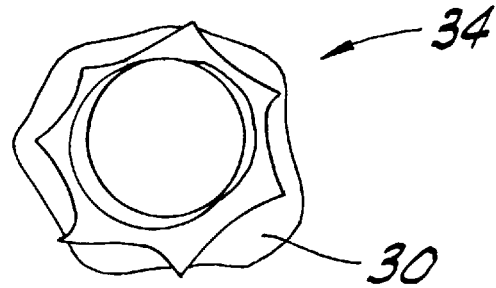
Figure 4B:
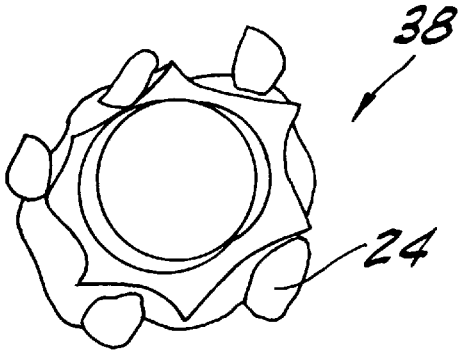

FIGS. 3b and 4b show particles 32 and 34 having particles 24 in contact with the layer 30 to form particles 36 and 38, respectively. The particles 24 contain an anhydrous material capable of binding with water.

Figure 5A:
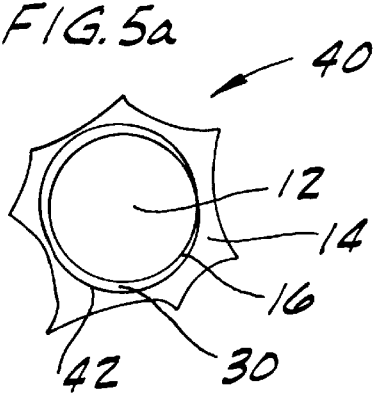
Figure 5B:
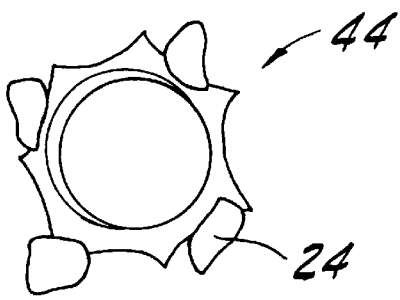

FIG. 5a illustrates a particle 40, another embodiment of the invention, in which the layer 30 containing the hydrophobic, water-soluble, water-degradable or water-swellable material contacts the outer surface 16 of the core 12. The acid releasing layer 14 contacts an outer surface 42 of the layer 30 such that the layer 30 separates the core 12 from the acid releasing layer 14 and delays diffusion of hydronium ions into the core. The core 12 comprised a particle as described herein, and the acid releasing layer 14 contains an acid releasing agent. In FIG. 5b, the particle 40 of FIG. 5a is contacted with the particles 24 to form a particle 44. When the acid releasing layer 14 is exposed to moisture, the acid releasing agent is hydrolyzed, releasing acid and hydronium ions which diffuse from the acid releasing layer to the layer 30. The hydronium ions do not diffuse into the core 12 until enough hydronium ions or moisture are present in the layer 30 to provide a pathway for interdiffusion between the layer 30 and the core. The layer 30 controls the release of gas by prolonging diffusion of hydronium ions into the core to delay their reaction with anions within the core as described above. Although the layers 14 and 30 are preferably continuous and substantially uniform, a particle 40 or 44 having discontinuous layers 14 and 30 of variable thickness provides acceptable, sustained release of a gas.

Figure 6A:
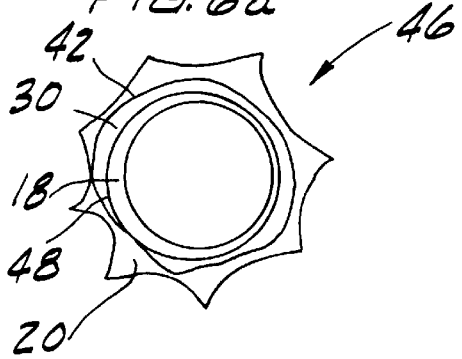
Figure 6B:
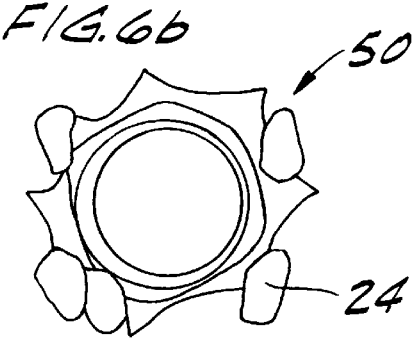

FIG. 6a illustrates a particle 46 in which the layer 30 containing the hydrophobic, water-soluble, water-degradable or water-swellable material contacts the outer surface 48 of the layer 18 containing a substantially water-insoluble silicate. The acid releasing layer 20 contacts an outer surface 42 of the layer 30 such that the layer 30 separates the coated core from the acid releasing layer 20 and delays diffusion of hydronium ions into the core. In FIG. 6b, the particle 46 of FIG. 6a is contacted with the particles 24 to form a particle 50. The acid releasing layer 20 contains an acid releasing agent, and the particles 24 contain an anhydrous material capable of binding with water. When the acid releasing layer 20 is exposed to moisture, the acid releasing agent is hydrolyzed, releasing acid and hydronium ions which diffuse from the acid releasing layer 20 to the layer 30. The hydronium ions do not diffuse into the layer 18 until enough hydronium ions or moisture are present in the layer 30 to provide a pathway for interdiffusion between the layer 30 and the layer 18. The layer 30 controls the release of gas by prolonging diffusion of hydronium ions into the layer 18 to delay their reaction with anions within the core as described above. Although the layers 18, 20 and 30 are preferably continuous and substantially uniform, a particle 46 or 50 having discontinuous layers 18, 20 and 30 of variable thickness provides acceptable, sustained release of a gas.

Figure 7A:
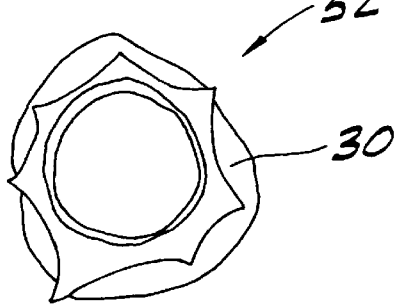
Figure 7B:
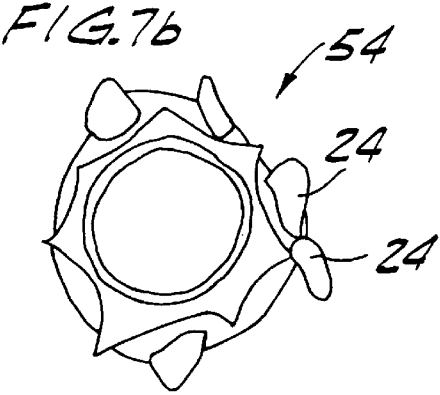

In another embodiment illustrated in FIG. 7a, the particle 40 as shown in FIG. 5a is surrounded by an outer layer 30 containing a hydrophobic, water-soluble, water-degradable or water-swellable material to form a particle 52. The outer layer 30 controls gas release by delaying diffusion of water into layer 14 until enough moisture is adsorbed by the layer 30 to provide a pathway for interdiffusion between the layers 14 and 30. The inner layer 30 also controls gas release by delaying diffusion of hydronium ions into the core 12 until enough hydronium ions or moisture are present in the layer 30 to provide a pathway for interdiffusion between the layer 30 and the core 12. In FIG. 7b, the particle 52 of FIG. 7a is contacted with the particles 24 to form a particle 54. Although the layers 14 and 30 are preferably continuous and substantially uniform, a particle 52 or 54 having discontinuous layers 14 and 30 of variable thickness provides acceptable, sustained release of a gas.

Figure 8A:
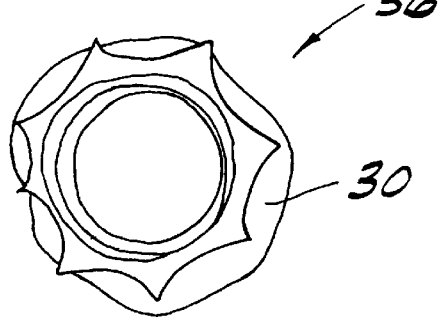
Figure 8B:
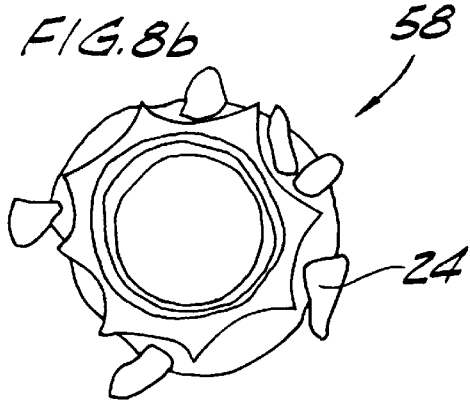

In another embodiment illustrated in FIG. 8a, the particle 46 as shown in FIG. 6a is surrounded by an outer layer 30 containing a hydrophobic, water-soluble, water-degradable or water-swellable material to form a particle 56. The outer layer 30 controls gas release by delaying diffusion of water into layer 20 until enough moisture is adsorbed by the layer 30 to provide a pathway for interdiffusion between the layers 20 and 30. The inner layer 30 also controls gas release by delaying diffusion of hydronium ions into the layer 18 and the core until enough hydronium ions or moisture are present in the layer 30 to provide a pathway for interdiffusion between the layer 30 and the layer 18. In FIG. 8b, the particle 56 of FIG. 8a is contacted with the particles 24 to form a particle 58. Although the layers 18, 20 and 30 are preferably continuous and substantially uniform, a particle 56 or 58 having discontinuous layers 18, 20 and 30 of variable thickness provides acceptable, sustained release of a gas.

The core 12 is substantially free of water as described above for the silicate particles. The layers 14, 18, 20 and 30 and the particles 24 are substantially free of water to avoid release of gas prior to use of the powder. For purposes of the present invention, the layers 14, 18, 20 and 30, and the particles 24 are substantially free of water if the amount of water in the powder does not provide a pathway for transmission of hydronium ions from the layer 14 or 20 to the core 12. Preferably, each of the layers 14, 18, 20 and 30, and the total particles 24 embedded in the outer layer of the particles 10, 22, 32, 34, 36, 38, 40, 44, 46, 50, 52, 54, 56 or 58 can include up to about 10 wt. % water and, more preferably up to about 5 wt. % water, without providing such a pathway for interdiffusion between the core 12 and the acid releasing layer 14 or 20. Insubstantial amounts of water can hydrolyze a portion of the acid releasing agent to produce acid and hydronium ions within the acid-releasing layer. The hydronium ions, however, do not diffuse into the core until enough water is present for transport of hydronium ions.

The powders of the invention can include coatings (i.e., additional layers) between the core 12 and the layers 14 or 20 or between the layers 14 or 20 and the outer surface of the powder so long as the coatings do not completely prevent the diffusion of hydronium ions from the acid-releasing layer 14 or 20 to the core 12 or diffusion of gas from the powder. Although discontinuous layers are acceptable, the additional layers are preferably continuous and substantially uniform. The powders preferably are about 0.1 microns to about 1 millimeter in size.

Powders including an Interpenetrating Network

In another embodiment of the invention as shown in FIG. 9a, a powder is comprised of a plurality of particles 60 containing an interpenetrating network 62. The interpenetrating network contains an amorphous, paracrystalline or crystalline solid solution, anions that are capable of reacting with hydronium ions to generate a gas, and an acid releasing agent. The solid solution of the interpenetrating network is preferably a substantially amorphous material. A substantially water-insoluble silicate preferably surrounds the interpenetrating network to minimize diffusion of the anions into the solution used to prepare the powder so as to minimize loss of anions needed to generate a gas. Alternatively, the solid solution of the interpenetrating network can contain a water-soluble silicate. For purposes of the present invention, an "interpenetrating network" is a material comprised of two or more phases in which at least one phase is topologically continuous from one free surface to another. The particles 60 are either solid (not shown) or hollow (FIG. 9a), and are generally substantially spherical. The powders preferably are about 0.1 microns to about 1 millimeter in size.

The powder can also include particles 24 which contact an outer surface of the particle 60 or are embedded in the particle as shown in FIG. 9b to form particle 64. The particles 24 contain an anhydrous material capable of binding with water.

When a particle 60 or 64 is exposed to ambient moisture or otherwise contacted with water, the water diffuses into the interpenetrating network 62. In a particle 64, the water binds to the particles 24 on the outer surface of the particle 64 before diffusing into the interpenetrating network 62. The acid releasing agent within the interpenetrating network is either an acid, a substance that can be hydrolyzed to an acid (i.e., a substance that reacts with the water that diffuses into the interpenetrating network to form an acid), or a mixture thereof. In either case, the acid in the interpenetrating network dissolves in the water that diffuses into the network, forming hydronium ions and a counterion. The reaction products of this hydrolysis reaction are hydronium ions and counterions when the reaction proceeds to completion, or hydronium ions, counterions, acid and water when the reaction is in equilibrium. The hydronium ions diffuse through the interpenetrating network until they contact and react with anions to generate a gas. The gas diffuses out of the particle 60 or 64 into the surrounding atmosphere for a period of up to about six months to affect materials situated near the powder. Powders that release at least about $1.0 \times 10^{-6}$ gram gas/cm$^3$ for a period of at least one day, one week, one month or six months can be formulated by the processes of the present invention for a variety of end uses, as described herein. Although the powders generally provide sustained release of a gas, the powders can be formulated so that gas is released during less than one day if desired for a particular end use.

The powder can also be prepared to further delay generation of the gas. The particle 60 can be surrounded by a layer 30 containing a hydrophobic, water-soluble, water-degradable or water-swellable material to form a particle 66 as shown in FIG. 10a. When the particle 60 coated with a water-soluble or water-degradable material is exposed to moisture, the water dissolves or degrades the material for a period of up to six months, preferably from several hours to one month, before water contacts the acid releasing agent. When the particle 60 coated with a water-swellable material is exposed to moisture, the water diffuses into the material and causes the material to expand for a period of up to six months, preferably from several hours to one month, before water contacts the acid releasing agent. Coating the particle 60 with a hydrophobic material also prolongs the diffusion of water into the interpenetrating network for a period of up to six months, preferably from several hours to one month. Gas release does not occur until enough moisture is transmitted by the hydrophobic layer 30 to provide a pathway for interdiffusion between the interpenetrating network and the layer 30. After the water contacts the acid releasing agent, gas release occurs according to the mechanism described above. Although the layer 30 is preferably continuous and substantially uniform, a particle 60 having a discontinuous layer 30 of variable thickness provides acceptable, sustained release of a gas. The particle 66 can also be contacted with particles 24 containing an anhydrous material capable of binding with water to form a particle 68 as shown in FIG. 10b.

The particles 24, 60 and 64 and the layer 30 are substantially free of water to avoid release of gas prior to use of the powder. For purposes of the present invention, the particles 24, 60 and 64 and the layer 30 are substantially free of water if the amount of water in the powder does not provide a pathway for transmission of hydronium ions from the acid releasing agent to the anions within the interpenetrating network. Preferably, each of the particle 60 or 64, the layer 30, and the total particles 24 embedded in the outer layer of the particle can include up to about 10 wt. % water and, more preferably up to about 5 wt. % water, without providing such a pathway for interdiffusion between the anions and the acid releasing agent within the interpenetrating network. Insubstantial amounts of water can hydrolyze a portion of the acid releasing agent to produce acid and hydronium ions within the interpenetrating network. The hydronium ions, however, do not diffuse through the network until enough water is present for transport of hydronium ions.

Powders including a Single Phase

In another embodiment of the invention, a powder is prepared from particles (not shown) comprised of a single phase amorphous, paracrystalline or crystalline solid solution. Preferably, the solid solution contains a water-soluble silicate, anions that are capable of reacting with hydronium ions to generate a gas, and an acid releasing agent.

The powder can also include particles containing an anhydrous material which contact an outer surface of the particle or are embedded in the particle. The anhydrous material is capable of binding with water.

When the powder is exposed to ambient moisture or otherwise contacted with water, the water diffuses into the single phase. If the powder includes the anhydrous particles, the water binds to the anhydrous particles on the outer surface of the powder before diffusing into the single phase. The acid releasing agent within the single phase is either an acid, a substance that can be hydrolyzed to an acid (i.e., a substance that reacts with the water that diffuses into the single phase to form an acid), or a mixture thereof. In either case, the acid in the single phase dissolves in the water that diffuses into the powder, forming hydronium ions and a counterion. The reaction products of this hydrolysis reaction are hydronium ions and counterions when the reaction proceeds to completion, or hydronium ions, counterions, acid and water when the reaction is in equilibrium. The hydronium ions diffuse through the single phase until they contact and react with anions to generate a gas. The gas diffuses out of the powder into the surrounding atmosphere for a period of up to about six months to affect materials situated near the powder. Powders that release at least about $1.0 \times 10^{-6}$ gram gas/cm$^3$ for a period of at least one day, one week, one month or six months can be formulated by the processes of the present invention for a variety of end uses, as described herein. Although the powders generally provide sustained release of a gas, the powders can be formulated so that gas is released during less than one day if desired for a particular end use.

The powder can also be prepared to further delay generation of the gas. The particles can be surrounded by a layer containing a hydrophobic, water-soluble, water-degradable or water-swellable material as described above.

The powder is substantially free of water to avoid release of gas prior to use of the powder. For purposes of the present invention, the powder is substantially free of water if the amount of water in the powder does not provide a pathway for transmission of hydronium ions from the acid releasing agent to the anions within the single phase. Preferably, each powder particle, the hydrophobic, water-soluble, water-degradable or water-swellable layer, and the total particles embedded in the outer layer of the particle can include up to about 10 wt. % water and, more preferably up to about 5 wt. % water, without providing such a pathway for interdiffusion between the anions and the acid releasing agent within the single phase. Insubstantial amounts of water can hydrolyze a portion of the acid releasing agent to produce acid and hydronium ions within the single phase. The hydronium ions, however, do not diffuse through the single phase until enough water is present for transport of hydronium ions.

The rate of gas release from any powder of the invention, activation of the powder to initiate gas release, and the release rate profile can be altered in various ways, such as by changing the temperature of the powder, changing the ambient humidity, changing the concentration of acid releasing agent, silicate, hydrophobic material, or water-soluble, water-degradable, or water-swellable material in the powder, adding a desiccant or humectant to the powder to control release of gas once the powder is exposed to moisture, changing the hydrophobicity of a hydrophobic acid releasing agent by changing the nature of the acid generative moiety therein, changing the powder microstructure, substituting alternative hydrophobic materials, anhydrous particles or zinc, magnesium, calcium, aluminum or other monovalent, divalent or multivalent salts, changing the method of processing the powder, or changing the order of addition of ingredients in preparing the powder.

Relative Proportions

Preferably, the powder of FIG. 1a or 1b comprises between about 10 wt. % and about 30 wt. % core, between about 30 wt. % and about 90 wt. % acid releasing layer 14, and up to about 60 wt. % of the particles 24. More preferably, the powder comprises between about 15 wt. % and about 25 wt. % core, between about 50 wt. % and about 85 wt. % acid releasing layer, and up to about 35 wt. % of the particles. In addition to the acid releasing agent, the acid releasing layer 14 may also include between about 2 wt. % and about 20 wt. % substantially insoluble silicate, preferably between about 2 wt. % and about 15 wt. %, and more preferably, between about 2 wt. % and about 10 wt. %.

Preferably, the powder of FIG. 2a or 2b comprises between about 10 wt. % and about 30 wt. % core, between about 2 wt. % and about 70 wt. % silicate-containing layer 18, between about 20 wt. % and about 88 wt. % acid releasing layer 20, and up to about 60 wt. % of the particles 24. More preferably, the powder comprises between about 15 wt. % and about 25 wt. % core, between about 2 wt. % and about 65 wt. % silicate-containing layer 18, between about 25 wt. % and about 80 wt. % acid releasing layer, and up to about 50 wt. % of the particles.

The powders of FIGS. 3a–8b preferably comprise between about 10 wt. % and about 30 wt. % core, between about 2 wt. % and about 70 wt. % silicate-containing layer 18, between about 20 wt. % and about 88 wt. % acid releasing layer 14 or 20, up to about 60 wt. % of the particles 24, and up to about 50 wt. % hydrophobic, water-soluble, water-degradable or water-swellable material.

More preferably, the powders of FIGS. 3a and 5a comprise between about 15 wt. % and about 25 wt. % core, between about 25 wt. % and about 50 wt. % acid releasing layer 14, and between about 30 wt. % and about 50 wt. % hydrophobic, water-soluble, water-degradable or water-swellable material in layer 30. The powders of FIGS. 3b and 5b preferably contain between about 15 wt. % and about 25 wt. % core, between about 25 wt. % and about 35 wt. % acid releasing layer 14, between about 20 wt. % and about 50 wt. % of the particles 24, and between about 10 wt. % and about 35 wt. % hydrophobic, water-soluble, water-degradable or water-swellable material in layer 30. The powders of FIGS. 4a and 6a preferably contain between about 15 wt. % and about 25 wt. % core, between about 2 wt. % and about 15 wt. % silicate-containing layer 18, between about 30 wt. % and about 40 wt. % acid releasing layer 20, and between about 30 wt. % and about 50 wt. % hydrophobic, water-soluble, water-degradable or water-swellable material in layer 30. The powders of FIGS. 4b and 6b preferably comprise between about 15 wt. % and about 25 wt. % core, between about 2 wt. % and about 10 wt. % silicate-containing layer 18, between about 25 wt. % and about 35 wt. % acid releasing layer 20, between about 20 wt. % and about 45 wt. % of the particles 24, and between about 10 wt. % and about 30 wt. % hydrophobic, water-soluble, water-degradable or water-swellable material in layer 30. The powder of FIG. 7a preferably contain between about 15 wt. % and about 25 wt. % core, between about 25 wt. % and about 35 wt. % acid releasing layer 14, and between about 10 wt. % and about 50 wt. % hydrophobic, water-soluble, water-degradable or water-swellable material in each of the layers 30. The powder of FIG. 7b preferably contains between about 15 wt. % and about 25 wt. % core, between about 25 wt. % and about 35 wt. % acid releasing layer 14, between about 15 wt. % and about 40 wt. % of the particles 24, and between about 10 wt. % and about 35 wt. % hydrophobic, water-soluble, water-degradable or water-swellable material in each of the layers 30. The powder of FIG. 8a preferably contains between about 15 wt. % and about 25 wt. % core, between about 2 wt. % and about 10 wt. % silicate-containing layer 18, between about 25 wt. % and about 35 wt. % acid releasing layer 20, and between about 10 wt. % and about 45 wt. % hydrophobic, water-soluble, water-degradable or water-swellable material in each of the layers 30. The powder of FIG. 8b preferably comprises between about 15 wt. % and about 25 wt. % core, between about 2 wt. % and about 10 wt. % silicate-containing layer 18, between about 25 wt. % and about 35 wt. % acid releasing layer 20, between about 15 wt. % and about 40 wt. % of the particles 24, and between about 10 wt. % and about 30 wt. % hydrophobic, water-soluble, water-degradable or water-swellable material in each of the layers 30.

When the acid releasing layer contains an inorganic acid releasing agent, the acid releasing layer preferably comprises between about 30 wt. % and 100 wt. % acid releasing agent and up to about 70 wt. % of inert salts such as a sulfate salt.

When the acid releasing layer contains an organic acid releasing agent, the acid releasing layer preferably comprises between about 50 wt. % and 100 wt. % acid releasing agent, up to about 50 wt. % diluent and up to about 20 wt. % dispersant, and, more preferably, between about 35 wt. % and about 65 wt. % acid releasing agent, between about 35 wt. % and about 45 wt. % diluent and between about 2 wt. % and about 12 wt. % dispersant.

When the powder includes one hydrophobic, water-soluble, water-degradable or water-swellable layer 30, the layer 30 preferably contains between about 10 wt. % and 100 wt. % hydrophobic, water-soluble, water-degradable or water-swellable material, up to about 80 wt. % diluent and up to about 20 wt. % dispersant, and, more preferably, between about 40 wt. % and about 90 wt. % hydrophobic, water-soluble, water-degradable or water-swellable material, between about 2 wt. % and about 50 wt. % diluent and between about 2 wt. % and about 15 wt. % dispersant.

When the powder includes two layers 30, the layer 30 separating the core from the acid releasing layer preferably contains between about 10 wt. % and 100 wt. % hydrophobic, water-soluble, water-degradable or water-swellable material, up to about 80 wt. % diluent and up to about 20 wt. % dispersant, and, more preferably, between about 40 wt. % and about 90 wt. % hydrophobic, water-soluble, water-degradable or water-swellable material, between about 2 wt. % and about 50 wt. % diluent and between about 2 wt. % and about 15 wt. % dispersant. The outer layer 30 preferably contains between about 10 wt. % and 100 wt. % hydrophobic, water-soluble, water-degradable or water-swellable material, up to about 80 wt. % diluent and up to about 20 wt. % dispersant, and, more preferably, between about 40 wt. % and about 90 wt. % hydrophobic, water-soluble, water-degradable or water-swellable material, between about 2 wt. % and about 50 wt. % diluent and between about 2 wt. % and about 15 wt. % dispersant.

Preferably, the powder 60 or 64 comprises between about 30 and 100 wt. % of an interpenetrating network, up to about 50 wt. % hydrophobic, water-soluble, water-degradable or water-swellable material, and up to about 60 wt. % of the particles 24. The interpenetrating network preferably is comprised of between about 10 and about 30 wt. % of a first phase containing a silicate and anions capable of reacting to generate a gas, between about 20 and about 88 wt. % of a second phase containing an acid releasing agent, and between about 2 and about 70 wt. % of a coating on the interpenetrating network comprised of a water-insoluble silicate. More preferably, the powder 60 or 64 comprises between about 40 and 100 wt. % of an interpenetrating network, up to about 50 wt. % hydrophobic, water-soluble, water-degradable or water-swellable material, and up to about 50 wt. % of the particles 24.

Preferably, the powder prepared from the single-phase particles comprises between about 30 and 100 wt. % of a single phase comprised of a silicate, an acid releasing agent, and anions capable of reacting to generate a gas, up to about 50 wt. % hydrophobic, water-soluble, water-degradable or water-swellable material, and up to about 60 wt. % of the anhydrous particles. More preferably, the powder comprises between about 40 and 100 wt. % of the single phase, up to about 50 wt. % hydrophobic, water-soluble, water-degradable or water-swellable material, and up to about 50 wt. % of the anhydrous particles.

When the powder 60 or 64 or the powder prepared from the single phase particles includes a hydrophobic, water-soluble, water-degradable or water-swellable layer 30, the layer 30 preferably contains between about 10 wt. % and 100 wt. % hydrophobic, water-soluble, water-degradable or water-swellable material, up to about 80 wt. % diluent and up to about 20 wt. % dispersant, and, more preferably, between about 40 wt. % and about 90 wt. % hydrophobic, water-soluble, water-degradable or water-swellable material, between about 2 wt. % and about 50 wt. % diluent and between about 2 wt. % and about 15 wt. % dispersant.

Gas Generated and Released

The gas released by the powder will depend upon the anions within the core. Any gas that is formed by reaction of a hydronium ion and an anion can be generated and released by the powder. The gas is preferably chlorine dioxide, sulfur dioxide, hydrogen sulfide, hydrocyanic acid, nitrogen dioxide, nitric oxide, nitrous oxide, carbon dioxide, dichlorine monoxide, or chlorine.

Chlorine dioxide gas is released if the core contains a source of chlorite anions. Suitable chlorite sources that can be incorporated into the core include alkali metal chlorites such as sodium chlorite or potassium chlorite, alkaline-earth metal chlorites such as calcium chlorite, or chlorite salts of a transition metal ion, a protonated primary, secondary or tertiary amine, or a quaternary amine such as ammonium chlorite, trialkylammonium chlorite, and quaternary ammonium chlorite. Suitable chlorite sources, such as sodium chlorite, are stable at processing temperatures in excess of about 90° C. when incorporated in the particles and powders of the present invention, allowing for processing at relatively high temperatures. Chlorine dioxide-releasing powders can be used to deodorize, enhance freshness, retard, prevent or control chemotaxis, retard, prevent or control biochemical decomposition, or to kill, retard, control or prevent the growth of bacteria, molds, fungi, algae, protozoa, and viruses.

Sulfur dioxide is released if the core contains bisulfite or sulfite anions. Bisulfite sources that can be incorporated into the core include alkali metal bisulfites such as sodium bisulfite or potassium bisulfite, alkaline-earth metal bisulfites such as calcium bisulfite, or bisulfite salts of a transition metal ion, a protonated primary, secondary or tertiary amine, or a quaternary amine. Such bisulfite salts dissociate within the core to form bisulfite anions and possibly sulfite anions. Sulfur dioxide gas-releasing powders can be used for food preservation (e.g. to inhibit biochemical decomposition such as browning of produce), disinfection, and inhibition of enzyme-catalyzed reactions. The powders can also be used for reduction of chlorine gas concentration in catalytic cycles where aluminum or iron powder is used to selectively scrub chlorine from a mixture of chlorine and chlorine dioxide. The powders are also useful in modified atmosphere packaging by placing the powder within a package and sealing the package to create a sulfur dioxide atmosphere within the package.

Hydrogen sulfide is released from a core containing hydrosulfide or sulfide anions. Acceptable sources of hydrosulfide anions include alkali metal hydrosulfides such as sodium hydrosulfide or potassium hydrosulfide, alkaline-earth metal hydrosulfides such as calcium hydrosulfide, or hydrosulfide salts of a transition metal ion, a protonated primary, secondary or tertiary amine, or a quaternary amine. Acceptable sources of sulfide anions include alkali metal sulfides such as sodium sulfide or potassium sulfide, alkaline-earth metal sulfides such as calcium sulfide, or sulfide salts of a transition metal ion, a protonated primary, secondary or tertiary amine, or a quaternary amine. Hydrogen sulfide gas-releasing powders can be used as a reducing agent or a sulfur source in the manufacture of chemicals, and as a polymerization inhibitor.

Chlorine gas and dichlorine monoxide are released from a core containing hypochlorite anions. Acceptable sources of hypochlorite anions include alkali metal hypochlorites such as sodium hypochlorite, alkaline-earth metal hypochlorites such as calcium hypochlorite, or hypochlorite salts of a transition metal ion, a protonated primary, secondary or tertiary amine, or a quaternary amine. Chlorine gas-releasing powders can be used in processing meat, fish and produce and as an insecticide. Dichlorine monoxide releasing powders can be used as a biocide.

Hydrocyanic acid is released from a core if it contains a source of cyanide anions. Suitable sources of cyanide anions include alkali metal cyanides such as sodium cyanide or potassium cyanide, alkaline-earth metal cyanides such as calcium cyanide, or cyanide salts of a transition metal ion, a protonated primary, secondary or tertiary amine, or a quaternary amine. Hydrocyanic acid gas-releasing powders can be used as a pesticide or a rodenticide.

Carbon dioxide gas is released if a core contains a source of bicarbonate or carbonate anions. Suitable bicarbonate sources that can be incorporated into the core include alkali metal bicarbonates such as sodium bicarbonate, potassium bicarbonate, or lithium bicarbonate, alkaline-earth metal bicarbonates, or bicarbonate salts of a transition metal ion, a protonated primary, secondary or tertiary amine, or a quaternary amine such as ammonium bicarbonate. Such bicarbonate salts may dissociate within the core to form bicarbonate anions and possibly carbonate anions. Carbon dioxide gas-releasing powders can be used in greenhouses by applying it to the soil surface to enrich the air surrounding plants. The carbon dioxide-releasing powders can also be used in modified atmosphere packaging by placing the powder within a package and sealing the package to create a carbon dioxide atmosphere within the package. The package can then be used to control respiration of produce, cut flowers or other plants during storage and transportation, or to retard, prevent or control biochemical decomposition of foods.

Nitrogen dioxide and nitric oxide are released from a core if it contains a source of nitrite anions. Suitable sources of nitrite anions include alkali metal nitrites such as sodium nitrite or potassium nitrite, alkaline-earth metal nitrites such as calcium nitrite, or nitrite salts of a transition metal ion, a protonated primary, secondary or tertiary amine, or a quaternary amine. Nitrogen dioxide or nitric oxide gas-releasing powders can be used to improve biocompatibility of biomaterials and for modified atmosphere packaging.

In some instances, powders containing two or more different anions are effective in controlling release of a gas. The powder, for example, can be prepared from silicate particles prepared by admixing a chlorite salt and a bisulfite salt with a solvent and a silicate to form a solution, and spray drying the solution to form the particle. If chlorine dioxide and sulfur dioxide are released in preparing the silicate particles or the powder, the sulfur dioxide reduces the chlorine dioxide to chlorite, controlling release of chlorine dioxide. The presence of bisulfite anions in the silicate particles also delays chlorine dioxide release from the silicate particles or the powder during storage to avoid reaction of chlorine dioxide with powder additives such as fragrances. Powders containing two or more different anions can also release two or more different gases at different rates for different purposes. For example, a powder containing bisulfite and chlorite anions may release sulfur dioxide for food preservation and chlorine dioxide for deodorization, freshness enhancement, control of chemotaxis, or control of microorganisms.

Components

Acid Releasing Agents

Any acid releasing agent that is capable of being hydrolyzed by ambient moisture and adhered onto a particle, incorporated in a coating to be applied to a particle, incorporated into an interpenetrating network containing anions and an amorphous, paracrystalline or crystalline solid solution, or incorporated into a single phase amorphous, paracrystalline or crystalline solid solution containing anions is acceptable for purposes of the present invention. Preferably, the acid releasing agent does not react with the core or solid solution in the absence of moisture, and does not exude or extract into the environment. Suitable acid releasing agents include carboxylic acids, esters, anhydrides, acyl halides, phosphoric acid, phosphate esters, trialkylsilyl phosphate esters, dialkyl phosphates, sulfonic acid, sulfonic acid esters, sulfonic acid chlorides, phosphosilicates, phosphosilicic anhydrides, carboxylates of poly α-hydroxy alcohols such as sorbitan monostearate or sorbitol monostearate, and phosphosiloxanes. Examples of such acid releasing agents include degradable polyesters such as polylactic acid, polyglycolic acid, polyacrylic acid and copolymers or blends thereof, poly-β-hydroxybutyrate, polylactone, and an anhydride or phosphate ester blended with or grafted to polypropylene, polyethylene or polystyrene, or trimethylsilyl phosphate esters of the formulae

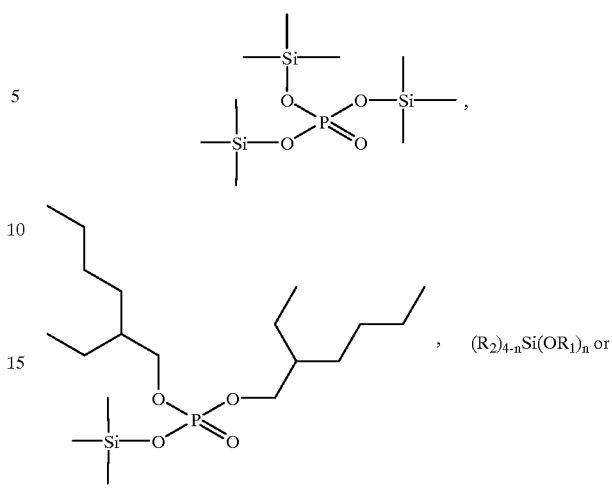

$CH_3SiOP(O)(OR)_2$ wherein R is a non-hydrogen bonding group, alkyl or aryl, $R_1$ and $R_2$ are alkyl, alkoxy or aryl and n is 1–4. Water-hydrolyzable acid releasing polymers or oligomers are preferred.

Linear or star like oligomers (e.g., a micelle like molecule with a lipid wall and a P—O—Si core), such as a phosphosilicic anhydride that is the reaction product of a phosphoric acid ester of a $C_2$ to $C_{27}$ organic compound and a silicate ester, are preferred acid releasing agents. Preferred phosphosilicic anhydrides of esters have the formula

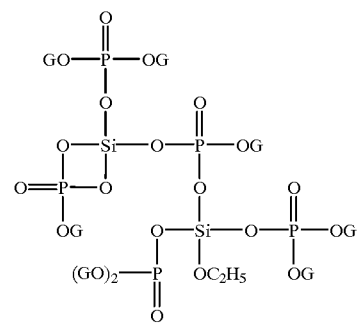

wherein G is a carboxylic acid ester of a polyhydric alcohol and a $C_4$ to $C_{27}$ hydrocarbon, which has the formula

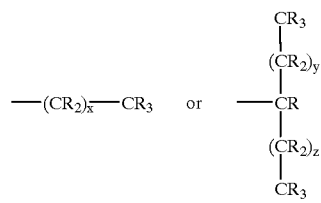

wherein each R is individually selected from hydrogen, hydroxy, alkyl, alkenyl, or —OC(O)R'; R' is a $C_4$ to $C_{27}$ alkyl or $C_4$ to $C_{27}$ alkenyl; x is an integer from 1 to 30; y is an integer from 0 to 30; and z is an integer from 0 to 30. Particularly preferred phosphosilicic anhydrides of polyol based esters include alkylene glycol fatty acid ester acid releasing waxes such as propylene glycol monostearate phosphosilicic acid releasing wax having the formula

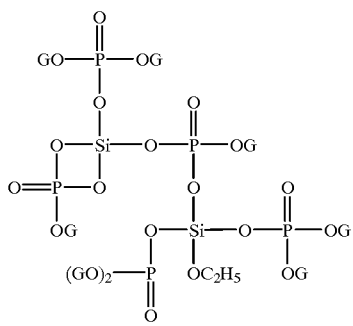

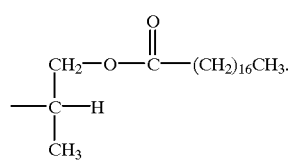

phosphosilicic anhydride of a glycerol based ester, known as LPOSI or glycerol monostearate acid releasing wax, has the formula

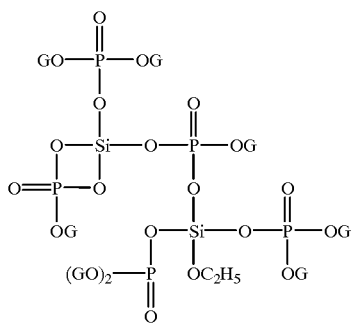

wherein G has the formula

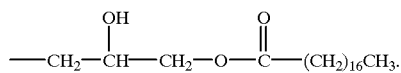

Other preferred acid releasing agents have the formulae:

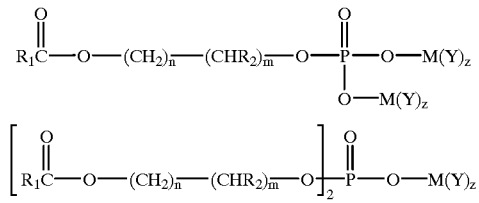

wherein $M(Y)_z$ is an oligomeric radical in which Y is a portion of a multifunctional oxide structure and M is a group IIIA, IVA, or IVB element such as titanium, aluminum, tin, or silicon; $R_1$ is an alkyl group; $R_2$ is methyl, ethyl, propyl, a methyl amido, or an ethyl amido group; m is 0, 1, 2 or 3; n is 0, 1, 2 or 3; and z is 2 or 3.

Acid anhydrides are also preferred acid releasing agents and include organic acid anhydrides, mixed organic acid anhydrides, homopolymers of an organic acid anhydride or a mixed inorganic acid anhydride, and copolymers of an organic acid anhydride or a mixed inorganic acid anhydride with a monomer containing a double bond. Preferred mixed inorganic acid anhydrides contain a phosphorus-oxygen-silicon bond. Preferred anhydrides include copolymers of maleic anhydride, methacrylic anhydride, acetic anhydride, propionic anhydride, or succinic anhydride, and vinyl, styrene or an alkene, such as maleic anhydride-styrene copolymers, or grafts thereof with olefins such as polypropylenes, polyethylenes, or polystyrenes. Copolymers of acid anhydrides and esters of lactic or glycolic acids can provide a rapid initial gas release rate followed by a slow release rate.

Preferred acid releasing polymers have a number average degree of polymerization of between about 10 and about 10,000, more preferably between about 50 and about 1000, and most preferably between about 100 and about 300, and include an acid releasing polymer copolymerized with a hydrophilic oligomer to compatibilize the acid releasing polymer with the chlorite anions and the hydrophilic material. A preferred acid releasing polymer is a copolymer of a phase compatibilizing oligomer such as polyvinylpyrrolidone, polyvinyl alcohol, polyanhydride, or polyacrylamide, and an acid such as lactic acid, glycolic acid, or other α-hydroxy acids or mixtures of these acids. Preferred polyanhydrides have the formula:

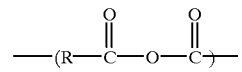

wherein R is:

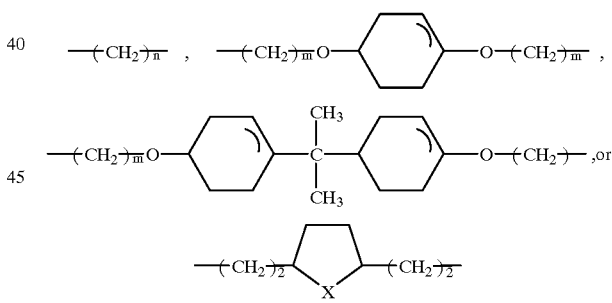

m is 1 or 2, n is an integer from 4 to 12, and X is O or N—$CH_3$. A particularly preferred acid releasing polymer is a terpolymer of polyvinylpyrrolidone, lactic acid and glycolic acid. Each of the lactic acid, glycolic acid and polyvinylpyrrolidone portions of the terpolymer preferably has a number average degree of polymerization of between about 1 and about 5,000, more preferably between about 5 and about 50 and, most preferably, between about 10 and about 30. The most preferred acid releasing polymer has the formula:

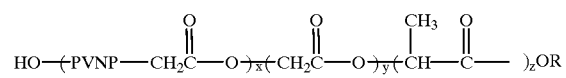

wherein PVNP has the formula:

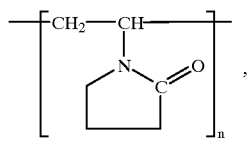

and R is a lower alkyl group or a lower alkyl ester, n is from 5 to 500, x is from 1 to 5,000, y is from 0 to 5,000, and z is from 0 to 5,000, provided that either y or z must be at least one. R is preferably a methyl group, n is preferably 5 to 100, and x, y and z are preferably 1 to 1,000. The optimum proportions of lactic acid, glycolic acid and polyvinylpyrrolidone in the terpolymer are selected based upon the adhesiveness, stiffness, or other properties required for a desired application of the composition. One of ordinary skill in the polymer art would have known how to optimize the proportions of lactic acid, glycolic acid and polyvinylpyrrolidone in the copolymer to obtain desired properties in the composition.

Inorganic acid releasing agents, such as polyphosphates, are the most preferred acid releasing agents because they form odorless powders having greater gas release efficiency as compared to powders containing an organic acid releasing agent. Suitable inorganic acid releasing agents include tetraalkyl ammonium polyphosphates, monobasic potassium phosphate ($KH_2PO_4$), potassium polymetaphosphate (($KPO_3)_x$ wherein x ranges from 3 to 50), sodium metaphosphates, borophosphates, aluminophosphates, silicophosphates, sodium polyphosphates such as sodium tripolyphosphate, potassium tripolyphosphate ($K_5P_3O_{10}$), sodium-potassium phosphate ($NaKHPO_4 \cdot 7H_2O$), and salts containing hydrolyzable metal cations such as zinc. Preferred sodium metaphosphates have the formula ($NaPO_3)_n$ wherein n is 3 to 10 for cyclic molecules and n is 3 to 50 for polyphosphate chains.

The preferred phosphosilicic anhydride acid releasing waxes are generally prepared by melting a carboxylic acid ester of a polyhydric alcohol, admixing phosphorus pentoxide into the melt, then admixing a silicate or silane into the melt, and cooling to solidify the resulting acid releasing wax. The carboxylic acid ester of a polyhydric alcohol is preferably a glycerol ester or glycol ester including, for example, an alkylene glycol carboxylate such as propylene glycol monostearate, glycerol monostearate, or glycerol distearate. Propylene glycol monostearate is most preferred because it does not foam excessively or obstruct nozzles or other fluid transport equipment when preparing the acid releasing wax, or the powders or when incorporating the powders into polymer films or other materials as end products. A substance that is capable of reacting with the silicate or silane to form P—O—Si or C(O)—O—Si bonds in the acid releasing wax can be substituted for phosphorus pentoxide, such as monostearyl diethylphosphate. A process for preparing a phosphosilicic anhydride acid releasing wax using monostearyl diethylphosphate can be performed with reference to Ralph Iler, "Chemistry of Silica: Solubility, Polymerization, Colloid and Surface Properties in Biochemistry," J. Wiley & Sons, N.Y., p. 297 (1979). Preferred silicates or silanes include tetraalkoxy silanes such as tetraethyl orthosilicate, and monoalkoxy silanes. The process of preparing the acid releasing waxes is described in copending Wellinghoff et al. U.S. Pat. No. 6,046,243, filed May 19, 1997 entitled "Compositions for Sustained Release of a Gas," and U.S. Pat. No. 5,965,264, filed Aug. 29, 1997 entitled "Powders Providing Controlled Sustained Release of a Gas," which are incorporated herein by reference.

Diluents

A diluent can be included in the acid releasing layer 14 or 20 or the interpenetrating network 62. The diluent is any hydrophobic material that can be incorporated into the interpenetrating network 62 or applied to the core or layer 18 and solidified to form a layer on the core or layer 18. Preferred diluents include microcrystalline wax, paraffin wax, synthetic wax such as chlorinated wax or polyethylene wax, or a polymer such as atactic polypropylene, polyolefin, or polyester, or polymer blends, multicomponent polymers such as copolymers, terpolymers or oligomers, or polymer alloys thereof. These diluents are commercially available from various sources. Preferred microcrystalline waxes suitable for use include the Astorwax microcrystalline waxes commercially available from Astor Wax Corp., Doraville, Ga. Diluents are preferably incorporated in the acid releasing layer or interpenetrating network if the acid releasing agent is organic but not hydrophobic.

Dispersants

The dispersant in the acid releasing layer 14 or 20 is any substance that minimizes agglomeration of the silicate particles during preparation of the powder, controls release of the gas from the powder, lowers the surface reactivity of the silicate particle, controls moisture penetration through the silicate particle, and does not react with the silicate particle. Substances having hydrophilic and hydrophobic portions are preferred. The hydrophilic portion of the substance can be absorbed by the surface of the silicate particle. The hydrophobic portion of the substance minimizes agglomeration of the silicate particles when the particles are mixed. Preferred dispersants that can be incorporated into the layer 14 or 20 or the interpenetrating network have a melting point not greater than 220° C., and include amides of carboxylates such as amide isostearates, polyvinyl acetates, polyvinyl alcohols, polyvinylpyrrolidone copolymers, polymers of alkylene oxides such as polyglycols, polyols, polyalkylene glycols (e.g., polyethylene glycols, polypropylene glycols, polybutylene glycols), alkoxypolyalkylene glycols such as methoxypolyethylene glycols, trifunctional polyethylene glycols, poly(ethylene-propylene)glycols, metallic, oligomeric or copolymeric olefinic carboxylic acids and/or fatty acids, polyethers, and metal carboxylates such as zinc isostearate, and derivatives (e.g., carboxylic acids such as fatty acids), blends and copolymers thereof. Some acid releasing agents, such as sodium polyphosphate, also act as a dispersant. Dispersants having a melting point greater than 50° C. are preferably admixed with the silicate particles before being admixed with the acid releasing agent. Suitable polyvinylpyrrolidone copolymers include copolymers of polyvinylpyrrolidone and hexadecane such as Ganex V-216, and copolymers of polyvinylpyrrolidone and eicosene such as Ganex V-220, which are commercially available from GAF Corp.

Hydrophobic, Water-Soluble, Water-Degradable or Water-Swellable Materials

The hydrophobic material of layer 30 is any hydrophobic material that can be applied to the core 12, the layer 14, 18 or 20 or the particle 60 and solidified to form a layer on the core 12, the layer 14, 18 or 20 or the particle 60. Suitable hydrophobic materials are the diluents described above.

Any water-soluble, water-degradable or water-swellable material that can be applied to the core 12, the layer 14, 18 or 20 or the particle 60 and solidified to form a layer on the core 12, the layer 14, 18 or 20 or the particle 60 can be used in the layer 30. Suitable water-soluble materials include sorbitol, polyvinylpyrrolidone, polyvinyl alcohol, polyalkylene glycols such as polyethylene glycol and polypropylene glycol, and carbohydrates such as monosaccharides (e.g., glucose, allose, altrose, mannose, gulose, idose, galactose, talose, ribose, arabinose, xylose, lyxose, erythrose, threose, fucose, rhamnose, and glucosamine), disaccharides (e.g., fructose, sucrose, maltose, lactose), polysaccharides (e.g., starches, modified starches, agarose, glycogen, cellulose, cellulose derivatives, and chitan), proteins, and modified proteins (e.g., soy protein). Suitable water-degradable materials include polylactic acids, polyglycolic acids, glycerol esters, polyhydroxyalkanoic acids, glycolipids, glycerides, phospholipids, polyesters, polyethers, polysorbates, lectins, polyureas, polyurethanes, ethylene vinyl acetate copolymers, polyhydroxyalkylates, polyanhydrides, polylactones, polysebacic acids, liposomes, fatty acids, carnauba wax, and blends, copolymers, terpolymers or derivatized polymers thereof. Water-swellable materials of the invention include polyvinyl alcohol and derivatives thereof, agarose, polyvinyl pyrrolidone and derivatives thereof, proteins such as gelatin, agar-agar, albumin and collagen, hydroxyproline polymers or oligomers, hydrophilic polyacrylate derivatives, polyethylene oxide and derivatives thereof, carboxyalkylcellulose and derivatives thereof, hydroxylated cellulose derivatives, alginic acid and derivatives thereof, acrylic polymers and copolymers, gums, polyacrylamides, starch graft copolymers, acrylate polymer polysaccharides, sodium starch glycolate, and indene-, styrene-, ethylene-, propylene-, butylene- or isobutylene-maleic anhydride copolymers.

Anhydrous Particles

The particles 24 embedded in the outer layer of the powder 26, 28, 36, 38, 44, 50, 54, 58 or 64 contain an anhydrous material capable of binding with water. The particles act as moisture scavengers to minimize premature hydrolysis of the acid releasing agent. Suitable anhydrous materials include sodium sulfate, calcium sulfate, calcium carbonate, magnesium sulfate, calcium chloride, moisture-depleted silica gel, alumina, zeolites, clays such as bentonite and kaolin, potassium permanganate, molecular sieves and oxygen-scavenging materials. The anhydrous particles are commercially available from numerous sources. The anhydrous particles are preferably between about 0.1 and about 300 microns in diameter.

The powder may also include conventional ingredients such as fragrances and flow enhancers such as sugars, talc and micronized polymers.

Process for Preparing Particles

The particles of the present invention are prepared by admixing an amorphous, paracrystalline or crystalline material, a solvent, a chlorite, bisulfite, sulfite, sulfide, hydrosulfide, nitrite, hypochlorite, or cyanide salt, and optionally, an inert core, to form a solution or suspension, and forming particles containing an amorphous, paracrystalline or crystalline solid solution from the solution or the suspension.

The silicate particles of the present invention are prepared by admixing a silicate, a solvent, a chlorite, bisulfite, sulfite, sulfide, bicarbonate, carbonate, hydrosulfide, nitrite, hypochlorite, or cyanide salt, and optionally, an inert core, to form a solution or a suspension, and forming the particles from the solution or the suspension.

Although the particles are preferably formed by spray drying the solution or suspension, the particles can also be formed by other solvent evaporation techniques, such as by mixing the solution or suspension with a water immiscible solvent, precipitating the particles and filtering to separate the particles from the solvent. The spray drying process generally occurs rapidly (e.g., within up to 30 seconds). While not being limited thereto, it is believed that spray drying or some other type of rapid evaporation of the solution or suspension forms a solid or hollow sphere composed of a solid solution, such as a substantially amorphous silicate matrix, in which the anions are uniformly dispersed and encapsulated. Such uniform dispersion and encapsulation enhances the thermal stability of the particles and a powder containing the particles. Powders containing the silicate particles are believed to release significantly more gas than powders containing crystalline cores. Gas release efficiencies of 75–100% are typical of the powders of the invention. The particles are stored in a dry atmosphere.

When preparing the solution or suspension, ultrasonic mixing, high-shear mixing, or any conventional homogenizing method can be used. The solvent used to form the solution or suspension is any liquid in which the silicate and the salt are soluble, such as water or a water solution of a water miscible organic material such as an alcohol, acetone or dimethylformamide.

Once the solution or suspension is formed, the particles can be formed by any method known in the art, such as conventional spray drying processes. If desired, the particles can then be vacuum dried or dried by any conventional method.

The wall thickness of a hollow particle can be altered by changing the process conditions, such as the feed rate, residence time, air flow rate, air temperature, flow direction in the dryer, or the type of nozzle or atomizer used in the spray drying process, or by changing the composition of the feed materials, such as the particle size, solids concentration, viscosity, surface tension or temperature of the feed solution.

The crystallinity of the silicate particles is altered by changing the silicate used in preparing the particles.

Any silicate that is soluble in water or a water solution of a water miscible organic material can be used in preparing the silicate particles of the invention. Suitable silicates include sodium silicate, sodium metasilicate, sodium sesquisilicate, sodium orthosilicate, borosilicates and aluminosilicates. Commercially available forms of such silicates suitable for use generally include sodium and potassium cations. The ratio of silicon measured as $SiO_2$ to alkali metal cation measured as $M_2O$ in the silicate particles, wherein M is selected from the group consisting of sodium and potassium, is between about 2.5 and about 3.5, preferably between about 3.0 and about 3.5, most preferably about 3.2.

Suitable salts used in preparing the silicate particles include an alkali metal chlorite, an alkaline-earth metal chlorite, a chlorite salt of a transition metal ion, a protonated primary, secondary or tertiary amine, or a quaternary amine, an alkali metal bisulfite, an alkaline-earth metal bisulfite, a bisulfite salt of a transition metal ion, a protonated primary, secondary or tertiary amine, or a quaternary amine, an alkali metal sulfite, an alkaline-earth metal sulfite, a sulfite salt of a transition metal ion, a protonated primary, secondary or tertiary amine, or a quaternary amine, an alkali metal sulfide, an alkaline-earth metal sulfide, a sulfide salt of a transition metal ion, a protonated primary, secondary or tertiary amine, or a quaternary amine, an alkali metal bicarbonate, an alkaline-earth metal bicarbonate, a bicarbonate salt of a transition metal ion, a protonated primary, secondary or tertiary amine, or a quaternary amine, an alkali metal carbonate, an alkaline-earth metal carbonate, a carbonate salt of a transition metal ion, a protonated primary, secondary or tertiary amine, or a quaternary amine, an alkali metal hydrosulfide, an alkaline-earth metal hydrosulfide, a hydrosulfide salt of a transition metal ion, a protonated primary, secondary or tertiary amine, or a quaternary amine, an alkali metal nitrite, an alkaline-earth metal nitrite, a nitrite salt of a transition metal ion, a protonated primary, secondary or tertiary amine, or a quaternary amine, an alkali metal hypochlorite, an alkaline-earth metal hypochlorite, a hypochlorite salt of a transition metal ion, a protonated primary, secondary or tertiary amine, or a quaternary amine, an alkali metal cyanide, an alkaline-earth metal cyanide, or a cyanide salt of a transition metal ion, a protonated primary, secondary or tertiary amine, or a quaternary amine. Preferred salts include sodium, potassium, calcium, lithium or ammonium salts of a chlorite, bisulfite, sulfite, sulfide, hydrosulfide, bicarbonate, carbonate, hypochlorite, nitrite, or cyanide. Commercially available forms of chlorite and other salts suitable for use, such as Textone (Vulcan Corp.), can contain additional salts and additives such as tin compounds to catalyze conversion to a gas.

A base or a filler can also be used in forming the solution or suspension when preparing the silicate particles. The base controls release of gas from the particle by reacting with hydronium ions that diffuse into the particle from an acid releasing layer or interdiffuse into the anion-rich areas of the particle to form a salt. When the base is depleted, excess hydronium ions then react with the anions within the particle to form a gas. The filler controls release of a gas by creating a barrier to diffusion of hydronium ions. The amount of base or filler within the core can be adjusted to alter the time period before gas is released from the particle. For example, the concentration of the base or filler can be increased if a longer delay of gas release is desired. The silicate particle preferably includes a base or filler if chlorite anions are present in the particle to stabilize the chlorite during preparation of the particle or a powder containing the particle.

Any base that reacts with a hydronium ion or any filler can be incorporated in the silicate particle. Suitable bases or fillers include, but are not limited to, an alkali metal bicarbonate such as lithium, sodium, or potassium bicarbonate, an alkali metal carbonate such as lithium, sodium or potassium carbonate, an alkaline-earth metal bicarbonate, an alkaline-earth metal carbonate such as magnesium or calcium carbonate, a bicarbonate salt of a transition metal ion, a protonated primary, secondary or tertiary amine, or a quaternary amine such as ammonium bicarbonate, a carbonate salt of a transition metal ion, a protonated primary, secondary or tertiary amine, or a quaternary amine, an alkali metal hydroxide such as lithium, sodium or potassium hydroxide, an alkaline-earth metal hydroxide such as calcium or magnesium hydroxide, a hydroxide salt of a transition metal ion, a protonated primary, secondary or tertiary amine, or a quaternary amine such as ammonium hydroxide, an alkali metal phosphate such as dibasic or tribasic phosphate salts, an alkaline-earth metal phosphate such as bicalcium or tricalcium phosphate, a phosphate salt of a transition metal ion, a protonated primary, secondary or tertiary amine, or a quaternary amine, an alkali metal sulfate such as sodium or potassium sulfate, an alkaline-earth metal sulfate such as calcium or magnesium sulfate, a sulfate salt of a transition metal ion, a protonated primary, secondary or tertiary amine, or a quaternary amine such as ammonium sulfate, an alkali metal sulfonate such as sodium sulfonate, an alkaline-earth metal sulfonate, or a sulfonate salt of a transition metal ion, a protonated primary, secondary or tertiary amine, or a quaternary amine, an alkali metal borate such as borax, an alkaline-earth metal borate such as magnesium orthoborate, or a borate salt of a transition metal ion, a protonated primary, secondary or tertiary amine, or a quaternary amine.

Processes for Preparing Powders

A powder of particles 10 as shown in FIG. 1a or particles 60 as shown in FIG. 9a is generally prepared by admixing the silicate particles described above with a solvent to form a slurry, admixing a zinc, magnesium, calcium, aluminum or other monovalent, divalent or multivalent salt and an acid releasing agent with the slurry to form a solids-containing suspension, and forming a powder from the solids-containing suspension.

A powder prepared from the single-phase particle or a powder containing an interpenetrating network comprised of a water-soluble silicate are generally prepared by admixing a silicate, a solvent, an acid releasing agent, and a chlorite, bisulfite, sulfite, sulfide, bicarbonate, carbonate, hydrosulfide, nitrite, hypochlorite, or cyanide salt to form a solution, and forming the powder from the solution.

Another method for preparing a powder of particles 10 or particles 60 includes admixing a silicate, a solvent, an acid releasing agent, and a chlorite, bisulfite, sulfite, sulfide, bicarbonate, carbonate, hydrosulfide, nitrite, hypochlorite, or cyanide salt, and optionally, an inert core, to form a solution or suspension, and forming the particles from the solution or suspension.

When preparing the slurry, ultrasonic mixing, high-shear mixing, or any conventional homogenizing method can be used to slurry the silicate particles. The solvent used to form the slurry is any liquid in which the zinc, magnesium, calcium, aluminum or other monovalent, divalent or multivalent salt is soluble, such as water or a water solution of a water miscible organic material such as an alcohol, acetone or dimethylformamide.

The zinc, magnesium, calcium, aluminum or other monovalent, divalent or multivalent salt and acid releasing agent can be added to the slurry simultaneously, or sequentially (i.e., addition of the zinc, magnesium, calcium, aluminum or other monovalent, divalent or multivalent salt before the acid releasing agent) to form the solids-containing suspension. When addition is simultaneous, a layer 14 containing an insoluble silicate and an acid releasing agent is formed as shown in FIG. 1a, or an interpenetrating network containing an insoluble silicate is formed as shown in FIG. 9a. When the zinc, magnesium, calcium, aluminum or other monovalent, divalent or multivalent salt is added to the slurry before the acid releasing agent, a layer 18 containing an insoluble silicate is formed around the core, or an interpenetrating network containing an insoluble silicate is formed as shown in FIG. 9a. An acid releasing layer 20 adheres to an outer surface of the layer 18 to form the powder 22 as shown in FIG. 2a. The silicate in the layer 14 or 18 or the interpenetrating network is formed by reaction of the zinc, magnesium, calcium, aluminum or other monovalent, divalent or multivalent salt with the silicate in the silicate particles, and is substantially insoluble in the solvent but permeable to water and hydronium ions.

Any soluble zinc, magnesium, calcium, aluminum or other monovalent, divalent or multivalent salt that will react with the silicate in the silicate particles to form an insoluble silicate in the layer 14 or 18 or the interpenetrating network can be used to form the powder. Suitable zinc, magnesium, calcium, aluminum or other monovalent, divalent or multivalent salts include zinc sulfate, zinc chloride, zinc ammonium chloride, zinc bromide, magnesium sulfate, magnesium chloride, magnesium bromide, magnesium calcium chloride, calcium sulfate, calcium chloride, calcium bromide, aluminum sulfate, aluminum ammonium chloride, aluminum chloride, aluminum potassium sulfate, or aluminum sodium sulfate, which react with the core to form zinc silicate, magnesium silicate, magnesium trisilicate, calcium silicate, or aluminum silicate.

Once the solids-containing suspension is formed, it can be spray dried to form a powder by any method known in the art including, for example, any known atomization methods such as nozzles or rotary discs. Typically, the inlet temperature and outlet temperature are maintained at about 300 to about 350° C. and about 100 to about 150° C., respectively. The powder may then be vacuum dried or dried by any conventional method. A powder of the particles 26 or 28 as shown in FIGS. 1b and 2b or a delayed-release powder containing particles 64 as shown in FIG. 9b can be prepared by admixing anhydrous particles with the particles 10, 22 or 60 and sintering or by hot spray coating the powder with anhydrous particles suspended in an emulsifier.

Powders of the particles 32 or 34 as shown in FIGS. 3a and 4a or delayed-release powders containing particles 60 as shown in FIG. 10a can be prepared by admixing the particles 10, 22 or 60 with a liquid containing a hydrophobic, water-soluble, water-degradable or water-swellable material to form a dispersion, and forming the powder from the dispersion. A powder of the particles 36, 38 or 68 as shown in FIGS. 3b, 4b and 10b can be prepared by admixing anhydrous particles with the particles 32, 34 or 60 and sintering or by hot spray coating the powder with anhydrous particles suspended in an emulsifier.

A powder of particles 40 as shown in FIG. 5a is generally prepared by admixing the core particles with a liquid containing a hydrophobic, water-soluble, water-degradable or water-swellable material to form a slurry, separating coated core particles from the slurry, drying the coated core particles, admixing the coated core particles with a solution containing a zinc, magnesium, calcium, aluminum or other monovalent, divalent or multivalent salt and an acid releasing agent to form a solids-containing suspension, and forming the powder from the solids-containing suspension. A powder of the particles 44 as shown in FIG. 5b can be prepared by admixing anhydrous particles with the powder and sintering or by hot spray coating the powder with anhydrous particles suspended in an emulsifier.

A powder of particles 46 as shown in FIG. 6a is generally prepared by admixing the core particles with a silicate solution to form a dispersion, separating encapsulated core particles from the dispersion, drying the encapsulated core particles, admixing the encapsulated core particles with a liquid containing a hydrophobic, water-soluble, water-degradable or water-swellable material to form a slurry, separating coated core particles from the slurry, drying the coated core particles, admixing the coated core particles with a solution containing an acid releasing agent to form a solids-containing suspension, and forming the powder from the solids-containing suspension. A powder of the particles 50 as shown in FIG. 6b can be prepared by admixing anhydrous particles with the powder and sintering or by hot spray coating the powder with anhydrous particles suspended in an emulsifier.

Powders of the particles 52 or 56 as shown in FIGS. 7a and 8a can be prepared by admixing the particles 40 or 46 with a liquid containing a hydrophobic, water-soluble, water-degradable or water-swellable material to form a dispersion, and forming the powder from the dispersion. A powder of the particles 54 or 58 as shown in FIGS. 7b and 8b can be prepared by admixing anhydrous particles with the powder and sintering or by hot spray coating the powder with anhydrous particles suspended in an emulsifier.

The morphology of any of the powders of the invention can be altered by changing the particle size, solids concentration or relative ratio of components, viscosity, surface tension or temperature of the feed solution, the feed rate, residence time, air flow rate, air temperature, flow direction in the dryer, or the type of nozzle or atomizer used in the spray drying process as is known in the art.

A powder of particles 10 can also be prepared by admixing the silicate particles with a liquid containing the acid releasing agent and silicate to form coated particles, cooling the coated particles, and fragmenting the cooled particles to form the powder. A powder of particles 22 is formed if the silicate particles are admixed with a liquid containing the silicate and cooled before being admixed with a liquid containing the acid releasing agent. A powder of particles 26 or 28 as shown in FIGS. 1b and 2b can be prepared by admixing anhydrous particles with the coated particles before cooling. The silicate particles can be dip-coated in a molten liquid, spray-coated with a liquid solution, or coated by other known processes.

A powder of particles 10 can also be prepared by admixing the silicate particles with particles containing an acid releasing agent and a silicate to form a particle mixture, sintering the mixture to form a product, cooling the product, and fragmenting the product to form the powder. A powder of particles 22 is formed by admixing the core particles with silicate-containing particles, sintering to form encapsulated core particles, admixing the encapsulated core particles with acid releasing particles to form a mixture, sintering the mixture to form a product, cooling the product, and fragmenting the product to form the powder. A powder of the particles 26 or 28 can be prepared by admixing anhydrous particles with the product and sintering before cooling. The acid releasing particles or the liquid containing the acid releasing agent can include a dispersant as described above to prevent agglomeration of the core particles.

A powder of the particles 32 or 34 as shown in FIGS. 3a and 4a can be made by preparing the particles 10 or 22 as described above and then admixing the particles 10 or 22 with a liquid containing a hydrophobic, water-soluble, water-degradable or water-swellable material to form a coated product, cooling the coated product, and fragmenting the coated product to form the powder. A powder of particles 36 or 38 as shown in FIGS. 3b and 4b can be prepared by admixing anhydrous particles with the coated product before cooling.

A powder of particles 32 or 34 can also be formed by admixing the particles 10 or 22 with particles containing a hydrophobic, water-soluble, water-degradable or water-swellable material to form a mixture, sintering the mixture to form a product, cooling the product, and fragmenting the product to form the powder. A powder of the particles 36 or 38 can be prepared by admixing anhydrous particles with the product and sintering before cooling.

A powder of particles 40 as shown in FIG. 5a can also be prepared by admixing the core particles with particles containing a hydrophobic, water-soluble, water-degradable or water-swellable material to form a first particle mixture, sintering the first particle mixture to form intermediate particles, admixing the intermediate particles with particles containing an acid releasing agent and a silicate to form a second particle mixture, sintering the second particle mixture to form a product, cooling the product, and fragmenting the product to form the powder. A powder of particles 46 as shown in FIG. 6a is prepared by admixing the core particles with silicate particles and sintering before admixing with the hydrophobic, water-soluble, water-degradable or water-swellable material to form a first particle mixture as described above. A powder of the particles 44 or 48 as shown in FIGS. 5b and 6b can be prepared by admixing anhydrous particles with the product and sintering before cooling.

A powder of particles 40 can also be prepared by admixing the core particles with a liquid containing a hydrophobic, water-soluble, water-degradable or water-swellable material to form coated core particles, cooling the coated core particles, fragmenting the coated core particles to form a core powder, admixing the core powder with a liquid containing the acid releasing agent to form coated particles, cooling the coated particles, and fragmenting the cooled particles to form the powder. A powder of particles 46 can also be prepared by admixing the core particles with a liquid containing a silicate, cooling and fragmenting before admixing the core particles with the liquid containing the hydrophobic, water-soluble, water-degradable or water-swellable material to form coated core particles as described above. A powder of particles 44 or 50 can be prepared by admixing anhydrous particles with the coated particles before cooling.

A powder of the particles 52 or 56 as shown in FIGS. 7a and 8a can be made by preparing the particles 40 or 46 as described above and then admixing the particles 40 or 46 with a liquid containing a hydrophobic, water-soluble, water-degradable or water-swellable material to form a coated product, cooling the coated product, and fragmenting the coated product to form the powder. A powder of particles 54 or 58 as shown in FIGS. 7b and 8b can be prepared by admixing anhydrous particles with the coated product before cooling.

A powder of particles 52 or 56 can also be formed by admixing the particles 40 or 46 with particles containing a hydrophobic, water-soluble, water-degradable or water-swellable material to form a mixture, sintering the mixture to form a product, cooling the product, and fragmenting the product to form the powder. A powder of the particles 54 or 58 can be prepared by admixing anhydrous particles with the product and sintering before cooling.

The powders of the invention can be prepared by the methods described above or by any conventional coating process, such as fluidization. In a fluidization method, the coating material is aerosolized by passing the material through small diameter nozzles into the chamber of the fluidized bed where it can impinge upon the fluidized core particles. Upon contact with the fluidized core particles, the powder is formed as the coating material solidifies. The particles can then be packaged in a dry sealed container. The particles can also be micronized to reduce their particle size and form a finer powder before being packaged. The powders of the invention can also be prepared using mechanical blending, mechanical-fluidized blending and other known powder preparation methods.

The anhydrous particles, silicate, and other ingredients can be manufactured by conventional processes and packaged in dry sealed containers, or can be purchased from various sources. The particles and other ingredients are stored in a dry atmosphere before being used in the powder preparation process.

Although the powders can be formulated as described above, it is preferred that the silicate particles are formed from an aqueous solution containing sodium silicate and an alkali metal chlorite or alkaline earth metal chlorite for release of chlorine dioxide. The salt used in forming the insoluble silicate is preferably magnesium sulfate. The acid releasing agent is preferably a polyphosphate such as sodium hexametaphosphate (available commercially as Calgon™ from Calgon). If an organic acid releasing agent is desired, the acid releasing layer preferably includes a microcrystalline wax, an oligomeric diluent or a low molecular weight polymeric diluent, and an acid releasing wax, such as propylene glycol monostearate phosphosilicic anhydride acid releasing wax. The layer 30 preferably contains sorbitol. The anhydrous particles 24 are preferably sodium sulfate or calcium sulfate.

Applications for the powders are numerous. The powders can be used in most any environment where exposure to moisture can occur. The powders can be formed into solids by molding or sintering. The powders can also be impregnated, melt processed, sintered, or otherwise incorporated into a variety of materials to provide films, fibers and coatings for a wide range of end use applications. The powders are particularly useful in preparing any injection-molded products, compression-molded products, thermal-formed products, or extrusion-formed products such as cast or blown films. The thermal stability of the powders allows for their use in injection molding processes.

Molded, Thermal-Formed or Extrusion-Formed Products Incorporating Powders of the Invention It has been discovered that the powders of the present invention can be incorporated into injection-molded, compression-molded, thermal-formed, or extrusion-formed products by contacting the powder with a percolation agent to form a percolation network within the product. The percolation network provides passages for transmission of moisture from the atmosphere surrounding the product to the gas-generating material within the network, increasing the amount of gas that can be generated during use of the product as compared to products formed without a percolation agent. Products formed without a percolation agent are generally more moisture impermeable and release less gas because less moisture is transmitted to the gas-generating material.

For purposes of the present invention, a "percolation network" is a material comprised of two or more phases in which at least one hydrophobic phase is topologically continuous from one free surface to another. The percolation network can be a co-continuous network, a discontinuous network, or a subsurface network. A "co-continuous network" is a percolation network in which all phases are topologically continuous from one free surface to another. A "discontinuous network" is a percolation network in which only the hydrophobic phase(s) is topologically continuous from one free surface to another. A "subsurface network" is a percolation network having a surface tension of less than 72 dynes/cm (i.e., hydrophobic surfaces) due to the formation of a skin or coating on its surfaces during processing. A subsurface network can be treated via corona discharge to add hydroxyl groups to one or more hydrophobic surfaces of the network, converting the hydrophobic surface to a hydrophilic surface.

Figure 18:
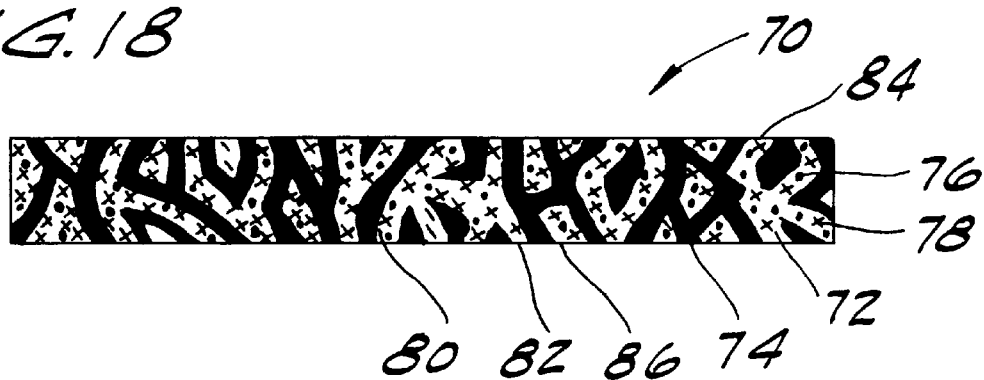
FIG. 18 is an exaggerated cross-sectional view of a film composed of a co-continuous network.

A co-continuous network 70 as shown in FIG. 18 contains a hydrophilic phase 72 and a hydrophobic phase 74. The hydrophilic phase includes a percolation agent 76 and a gas-generating material 78. The network includes passages 80 which extend throughout the network and terminate in openings 82 at surfaces 84 and 86 of the network. The passages provide pathways for transmission of moisture from the atmosphere surrounding the network to the gas-generating material within the network. The passages are needed to improve moisture penetration which may otherwise be hindered by the hydrophobic phase(s) of the network.

Figure 19:
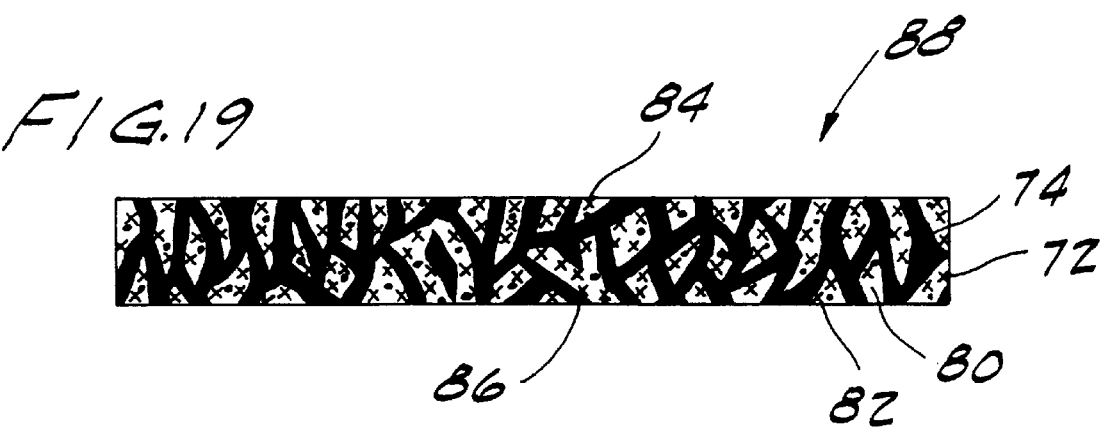
FIG. 19 is an exaggerated cross-sectional view of a film composed of a discontinuous network.

A discontinuous network 88 as shown in FIG. 19 contains the hydrophilic phase continuous 72 and the hydrophobic phase 74. The network includes passages 80 which extend throughout the network and terminate in openings 82 at either surface 84 or 86 of the network. The passages provide pathways for transmission of moisture from the atmosphere surrounding the network to the gas-generating material within the network. The hydrophobic phase of the percolation network contains any hydrophobic wax, polymer or multicomponent polymer such as a copolymer, a terpolymer or an oligomer, and polymer alloys or blends thereof. Suitable hydrophobic waxes include microcrystalline wax, paraffin wax, and synthetic wax such as chlorinated wax or polyethylene wax. Suitable polymers include polyolefins such as polyethylene and polypropylene, polyvinyl chloride, polyurethanes, metallocene polymers, polyesters, polyacrylic esters, acrylic, polystyrene, polycarbonates, polyamides, polyester amides, ethylene-vinyl acetate copolymers, ethylene-methacrylate copolymers, and polyacetals.

A hydrophobic plasticizer may be included in the hydrophobic phase to improve miscibility. For example, a dioctyl phthalate plasticizer can be included if polyvinyl chloride is selected as the hydrophobic material. A hydrophobic plasticizer is also preferably included when a polyolefin is used. When a hydrophobic plasticizer is included, it can phase separate with the hydrophilic phase to form a discontinuous network having hydrophobic phases that are topologically continuous from one free surface to another.

The hydrophilic phase contains the percolation agent and the gas-generating material. The percolation agent is any hydrophilic material that, when in direct contact with a gas-generating material, forms a percolation network with the hydrophobic phase but does not cause premature activation of the gas-generating material to release a gas. For example, ethylene glycol and glycerin cannot be used as percolation agents because they activate the gas-generating material as moisture does. Until the present invention, it was believed that all hydrophilic percolation agents would cause such premature activation of the gas-generating material. However, it has been discovered that many hydrophilic materials can perform as percolation agents without activating the gas-generating agent. Suitable percolation agents include organic humectants such as polyalkylene glycols (e.g., polyethylene glycol, polypropylene glycol), ethylene vinyl alcohol, polyvinyl alcohol, vinylpyrollidone, N-methyl pyrollidone, polyvinylpyrollidine, polysaccharides (e.g., polysaccharides composed of glucose, fructose and alcohols thereof and mannitol) and derivatives, copolymers or combinations thereof, inorganic humectants such as alkali metal and alkaline earth metal salts (e.g., magnesium sulfate, sodium sulfate, calcium chloride), super absorbent acrylates, super absorbent starches, super absorbent resins, antistatic agents, and processing aids such as plasticizers, lubricants, and foaming agents (e.g., surfactants).

The gas-generating material in the hydrophilic phase is a powder of the present invention or another moisture-activated, gas-releasing powder such as those described in copending U.S. Pat. Nos. 6,046,243, 5,888,528, and 5,922,776. Suitable gas-releasing powders include those comprised of a hydrophobic material containing an acid releasing agent as described above, and a hydrophilic material containing anions that are capable of reacting with hydronium ions to generate a gas as described above. The hydrophilic and hydrophobic materials are adjacent and substantially free of water, and the hydrophilic material is capable of generating and releasing the gas after hydrolysis of the acid releasing agent. The hydrophobic material can also include diluents as described above or plasticizers such as succinamide, formamide, N-methylacetamide, isopropylacrylamide-acrylamide or N-methyl formamide. The hydrophilic material can be composed entirely of a source of anions which react with hydronium ions to form the gas or can comprise the anion source in combination with another hydrophilic material, such as an amine, an amide or an alcohol, or a compound containing amino, amido or hydroxyl moieties and having a high hydrogen bonding density. In one embodiment, the hydrophilic material is particles containing anions that are capable of reacting with hydronium ions to generate a gas. The hydrophobic material is a hydrophobic core having the particles on a surface thereof.

Another suitable gas-releasing powder includes an acid releasing polymer as described above, a hydrophilic material, and anions that are capable of reacting with hydronium ions to generate a gas as described above. Each component of the composition has a particle size of not more than about 1,000 angstroms. The composition is substantially free of water and capable of generating and releasing the gas after hydrolysis of the acid releasing polymer. Any hydrophilic material that forms a solution with the anions and counterions and the acid releasing polymer is acceptable, such as an amide, an amine, or a polyhydric alcohol.

Yet another suitable gas-releasing powder includes a hydrophilic core, a hydrophobic layer on an outer surface of the hydrophilic core, and particles in contact with the hydrophobic layer. The hydrophobic layer contains an acid releasing agent as described above and may contain microcrystalline wax, paraffin wax, synthetic wax, or a polymer such as atactic polypropylene, polyolefin, or polyester, or polymer blends, multicomponent polymers such as copolymers or terpolymers, or polymer alloys thereof. The particles contain an anhydrous material capable of binding with water, such as sodium sulfate, calcium sulfate, ferrous sulfate, magnesium sulfate, calcium chloride, moisture-depleted silica gel, alumina, zeolites, clays such as bentonite and kaolin, potassium permanganate, molecular sieves and oxygen-scavenging salts. The core, the particles, and the hydrophobic layer are substantially free of water, and the core is capable of generating and releasing a gas after hydrolysis of the acid releasing agent. The hydrophilic core of the powder contains a salt composed of anions, which react with hydronium ions to form the gas, and counterions.

Conventional film forming additives can be added to the hydrophobic and hydrophilic materials as needed. Such additives include crosslinking agents, UV stabilizers, flame retardants, emulsifiers and compatibilizers.

The percolation networks of the present invention preferably contain between about 0.05 wt. % and about 50 wt. % percolation agent, between about 0.25 wt. % and about 70 wt. % gas-generating material, between about 20 wt. % and about 99.7 wt. % hydrophobic material, and up to about 50 wt. % hydrophobic plasticizer. More preferably, the percolation network contains between about 0.05 wt. % and about 5 wt. % percolation agent, between about 0.5 wt. % and about 50 wt. % gas-generating material, between about 50 wt. % and about 99.45 wt. % hydrophobic material, and up to about 50 wt. % hydrophobic plasticizer. When the percolation agent is an organic humectant such as polyethylene glycol, the percolation network preferably contains between about 0.05 wt. % and about 50 wt. % organic humectant, between about 0.25 wt. % and about 50 wt. % gas-generating material, between about 50 wt. % and about 99.7 wt. % hydrophobic material, and up to about 50 wt. % hydrophobic plasticizer, and more preferably, between about 0.05 wt. % and about 30 wt. % organic humectant, between about 0.5 wt. % and about 50 wt. % gas-generating material, between about 50 wt. % and about 75 wt. % hydrophobic material, and up to about 50 wt. % hydrophobic plasticizer. When the percolation agent is an inorganic humectant such as sodium sulfate, calcium chloride or magnesium sulfate, the percolation network preferably contains between about 15 wt. % and about 50 wt. % inorganic humectant, between about 0.25 wt. % and about 50 wt. % gas-generating material, between about 50 wt. % and about 84.75 wt. % hydrophobic material, and up to about 50 wt. % hydrophobic plasticizer, and more preferably, between about 15 wt. % and about 30 wt. % inorganic humectant, between about 0.5 wt. % and about 50 wt. % gas-generating material, between about 50 wt. % and about 75 wt. % hydrophobic material, and up to about 50 wt. % hydrophobic plasticizer. The amount of each component used to form the percolation network can be readily selected by one of ordinary skill in the art upon considering the intended use of the product.

The percolation networks can be made by any conventional polymer processing method. For example, powders of the percolation agent, gas-generating material, and hydrophobic material ingredients can be mixed together in a mixer, such as a Henschel mixer, and fed to an extruder or molding apparatus operated at a temperature not exceeding about 200° C. to form a melt. The melt can be cast-extruded as a film, formed into pellets using dry air cooling on a vibrating conveyer, or formed into a desired shape by conventional injection-molding, thermal-forming, or compression-molding methods. A hydrophobic plasticizer can optionally be added to the powder mixture to reduce the viscosity of the melt and increase the mixing compatibility of the hydrophobic material and the percolation agent. The percolation agent is miscible with the hydrophobic material when the melt is formed, but separates to form a hydrophilic phase as the melt solidifies, resulting in fine, capillary-like passages containing the gas-generating material throughout the percolation network.

In a preferred embodiment, powders of the percolation agent and the gas-generating material are blended together before the hydrophobic powder is introduced to ensure intimate contact between the percolation agent and the gas-generating material. The composition is prepared by admixing the percolation agent and the gas-generating material to form a powdered mixture, admixing the powdered mixture with the hydrophobic material to form a blend, heating the blend to form a melt, and cooling the melt to form the composition, which is a co-continuous network or a discontinuous network containing passages formed by the percolation agent. The passages are capable of transmitting moisture to the gas-generating material to generate and release a gas.

In another preferred embodiment, powders of the percolation agent and the gas-generating material are mixed together and added to a molten hydrophobic material. The composition is prepared by admixing the percolation agent and the gas-generating material to form a powdered mixture, admixing the powdered mixture with a melted hydrophobic material to form a melt, and cooling the melt to form the composition, which is a co-continuous network or a discontinuous network containing passages formed by the percolation agent. The passages are capable of transmitting moisture to the gas-generating material to generate and release a gas. Alternatively, a percolation agent powder can be mixed into the molten hydrophobic material before addition of the gas-generating powder to form the melt.

The percolation networks can be applied on a surface as a film by using well known hot melt, dip coat, spray coat, curtain coat, dry wax, wet wax, and lamination processes.

Use of Powders of the Invention

Gas-releasing powders can be used to retard, kill, prevent or control microbiological contamination on a surface of a material, within the material or in the atmosphere surrounding the material by exposing a surface of a material to a powder of the invention, and exposing the surface to moisture to generate and release a biocidal gas from the powder into the atmosphere surrounding the surface. In an alternative embodiment, microbiological contamination is retarded, killed, prevented or controlled on a surface of a material, within the material or in the atmosphere surrounding the material by placing the material adjacent a powder of the invention, and exposing the powder to moisture to release a biocidal gas from the powder into the atmosphere surrounding the material.

Gas-releasing powders can be used to retard, prevent or control biochemical decomposition on a surface of a material or within the material by exposing a surface of a material to a powder of the invention, and exposing the surface to moisture to generate and release a biochemical decomposition-inhibiting gas from the powder into the atmosphere surrounding the surface. In an alternative embodiment, biochemical decomposition is retarded, prevented or controlled on a surface of a material or within the material by placing the material adjacent a powder of the invention, and exposing the powder to moisture to release a biochemical decomposition-inhibiting gas from the powder into the atmosphere surrounding the material. The material is preferably produce such as fruits or vegetables, or other food. The food is preferably stored or transported in modified atmosphere packaging to extend the shelf life of the food by retarding, preventing or controlling biochemical decomposition or microbiological contamination.

The gas-releasing powders can also be used to control respiration of a material by exposing a surface of a material to a powder of the invention, and exposing the surface to moisture to generate and release a respiration-controlling gas from the powder into the atmosphere surrounding the surface. In an alternative embodiment, respiration of a material is controlled by placing the material adjacent a powder of the invention, and exposing the powder to moisture to release a respiration-controlling gas from the powder into the atmosphere surrounding the material. The material is preferably fruits, vegetables, flowers, or other plants. Control of respiration of foods and flowers is generally accomplished by storing and transporting the food or flowers in modified atmosphere packaging or selective gas permeable packaging.

The gas-releasing powders can also be used to deodorize a surface of a material or the atmosphere surrounding the material or enhance freshness of the material by exposing a surface of a material to a powder of the invention, and exposing the surface to moisture to generate and release a deodorizing gas from the powder into the atmosphere surrounding the surface. In another embodiment, a surface of a material or the atmosphere surrounding the material is deodorized or the freshness of the material is improved by placing the material adjacent to the powder, and exposing the powder to moisture to release a deodorizing gas from the powder into the atmosphere surrounding the material.

The gas-releasing powders can also be used to retard, prevent or control chemotactic attraction of an organism to a material by exposing a surface of a material to a powder of the invention, and exposing the surface to moisture to generate and release an odor-masking or odor-neutralizing gas from the powder into the atmosphere surrounding the surface. In another embodiment, chemotactic attraction of an organism to a material is retarded, prevented or controlled by placing the material adjacent to the powder, and exposing the powder to moisture to release an odor-masking or odor-neutralizing gas from the powder into the atmosphere surrounding the material.

In the above methods, the surface of the material or the entire material can be impregnated or coated with the powder, the powder can be admixed with the material, the powder can be enclosed within a gas-permeable container, or the material and the powder can be enclosed within a container. When the powder is enclosed within a container, the container can be hermetically sealed, or partially sealed such that some gas leaks from the container.

The chlorine dioxide-releasing powder, for example, can be impregnated into containers used to store food products, soap, laundry detergent, documents, clothing, paint, seeds, medical instruments, devices and supplies, personal care products, medical or biological waste, athletic shoes, ostomy bags, footwear, and refuse. A packet, sachet bag, "tea bag" or other gas-permeable container of the powder can be included in a storage container to provide a chlorine dioxide microatmosphere upon activation. The chlorine dioxide-releasing powder can also be impregnated into a paper or polymeric material (e.g., a shower mat, shoe liners, inserts or insoles, bandage material, a meat cutting board, a food wrapper, a food packaging tray, or a seed packet); incorporated into a wax or polymeric coating applied to paperboard containers or other surfaces; incorporated into films such as packaging films; formed into porous parts to sterilize water; admixed with a material to create a microatmosphere of chlorine dioxide about the material (e.g., soil); or admixed with other powders to kill microorganisms, enhance freshness or deodorize (e.g., foot powders, bath powders, powders used in treating jock itch, powders for treating soft surfaces such as carpet powders, desiccants for moisture removal).

The powders can also be admixed with binders or other conventional tabletting materials to form tablets that can be dissolved in water at the point of use to release chlorine dioxide for flower preservation, surface disinfection, sterilization of medical devices, or use as a mouthwash.

In addition to deodorization to neutralize malodors, the powders can be used to retard, prevent or control chemotaxis (i.e., the attraction of a living organism to a chemical substance). For example, odors from food can attract insects to the food. When the food is adjacent a powder of the invention that releases an odor-masking gas, the odor released from food is indistinct or imperceptible to the insects. The powders of the invention can also be used to release an odor-neutralizing gas so that the odor released from food is reduced or eliminated and insects are not attracted to the food.

The powders are also especially suitable for use in animal feeds. During preparation and handling, animal feeds for monogastric animals, such as chickens, swine, cats, dogs, rabbits, rats, mice and the like, are often contaminated with bacteria which infect the animal. If the powders of the present invention are formed from edible components, including edible protein coatings, the powders can be incorporated into the animal feed during any stage of production, before transportation or storage of the feed, or before use of the feed so that the chlorine dioxide will reduce or eliminate the bacteria within the feed. The controlled, sustained release powders also reduce the bacterial load in the intestines of such monogastric animals.

The following examples are presented to describe preferred embodiments and utilities of the present invention and are not meant to limit the present invention unless otherwise stated in the claims appended hereto.

EXAMPLE 1

Preparation of Silicate Particles 50 liters of a sodium silicate aqueous solution ($SiO_2/Na_2O$ ratio=3.22; 38.3% solids) was placed in a vessel equipped with a mechanical stirrer. 20 liters of a 10% sodium chlorite aqueous solution was added with vigorous stirring. The resulting solution was immediately spray dried in a commercial spray drying unit. The inlet temperature was set at 350° C., the outlet temperature was maintained at 150° C., the feed solution flow rate was 100 ml/min, and the atomizing gas was delivered at a ratio of 60:1 to the feed solution. The drying air was conveyed at a rate of 200 kg air/hour. The silicate particles so produced were dried to less than about 4 wt. % water in a vacuum oven (100° C./30 in. Hg vacuum) and stored in a dry atmosphere.

Figure 11:
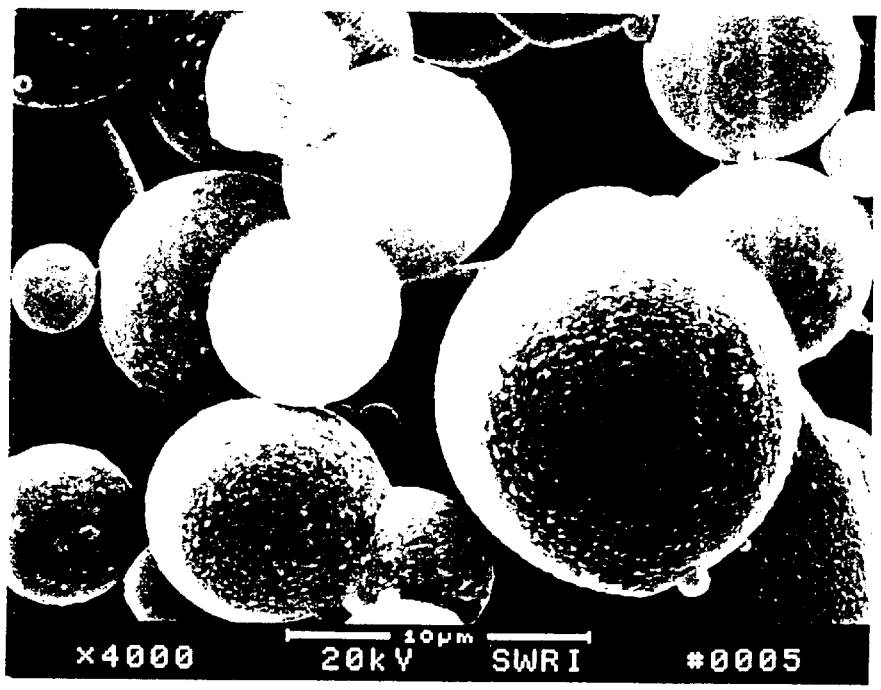
FIGS. 11–13 are photomicrographs of silicate particles and powders of the present invention.

The silicate particles prepared by this process are illustrated in FIG. 11, which shows generally spherical silicate particles of variable size.

EXAMPLE 2

Three Step Powder Preparation Process 25 kg of the silicate particles of Example 1 were slurried into 100 liters of a 50% magnesium sulfate heptahydrate ($MgSO_4 \cdot 7H_2O$) aqueous solution. 100 liters of a 30% sodium polyphosphate (($NaPO_3)_x$) aqueous solution was then added with vigorous stirring. The resulting slurry was immediately spray dried in a commercial spray drying unit. The inlet temperature was set at 350° C., the outlet temperature was maintained at 150° C., the feed solution flow rate was 100 ml/min, and the atomizing gas was delivered at a ratio of 60:1 to the feed solution. The drying air was conveyed at a rate of 200 kg air/hour. The product was somewhat moist (4–8% water) and was further dried immediately to below 1% water in a vacuum oven (100° C./30 in. Hg vacuum) and stored in a dry atmosphere.

EXAMPLE 3

Two Step Powder Preparation Process 25 kg of the silicate particles of Example 1 were slurried into 200 liters of an aqueous solution containing 25% magnesium sulfate heptahydrate ($MgSO_4 \cdot 7H_2O$) and 15% sodium polyphosphate (($NaPO_3)_x$) with vigorous stirring. The resulting slurry was immediately spray dried in a commercial spray drying unit. The inlet temperature was set at 350° C., the outlet temperature was maintained at 150° C., the feed solution flow rate was 100 ml/min, and the atomizing gas was delivered at a ratio of 60:1 to the feed solution. The drying air was conveyed at a rate of 200 kg air/hour. The product was somewhat moist (4–8% water) and was further dried immediately to below 1% water in a vacuum oven (100° C./30 in. Hg vacuum) and stored in a dry atmosphere.

Figure 12:
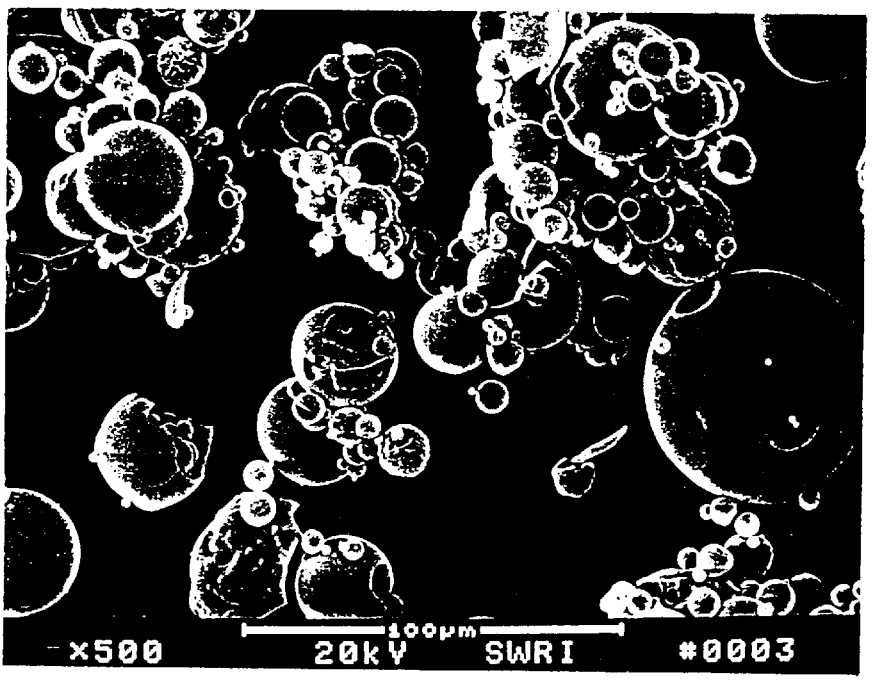
Figure 13:
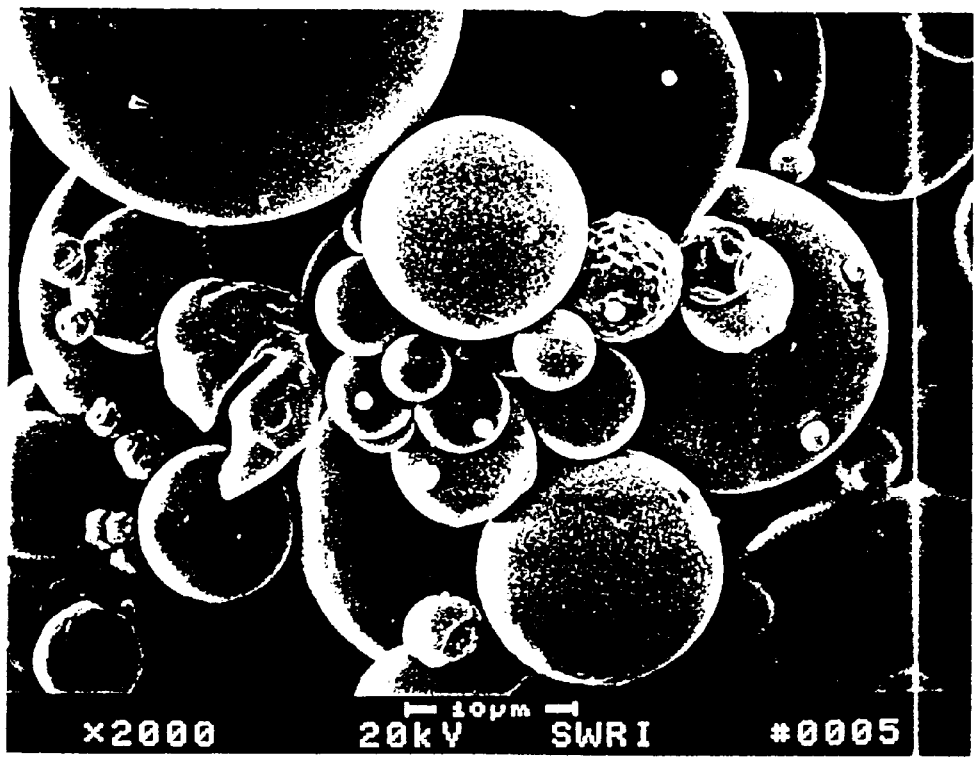

The powder prepared by this process is illustrated in FIGS. 12 and 13. These photomicrographs show generally spherical powder particles of variable size. Many of the powder particles are smooth or lamellar in appearance, and some are hollow.

Figure 14:
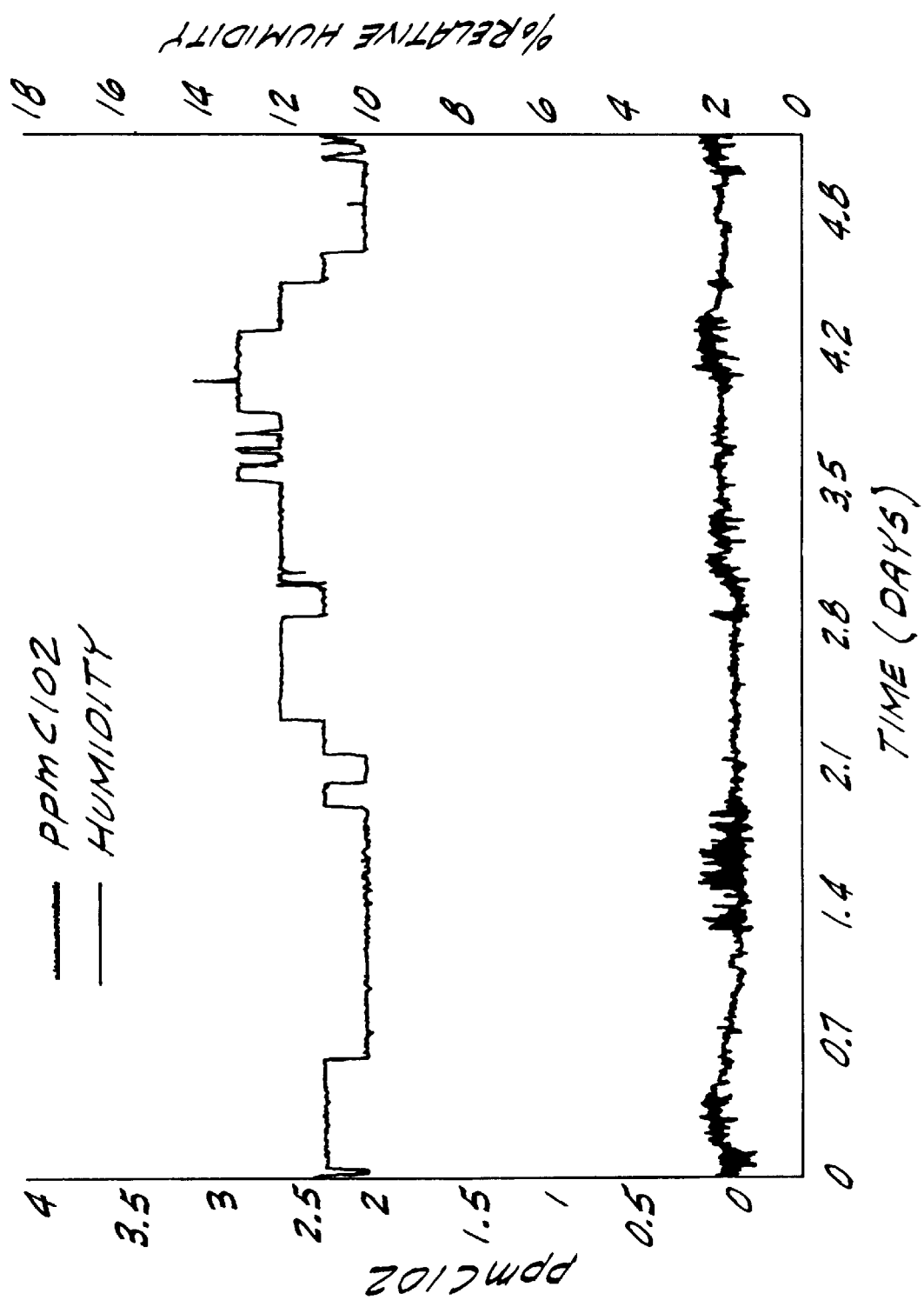
FIGS. 14 and 15 are plots of chlorine dioxide concentration and humidity as a function of time for a powder composition.
Figure 15:
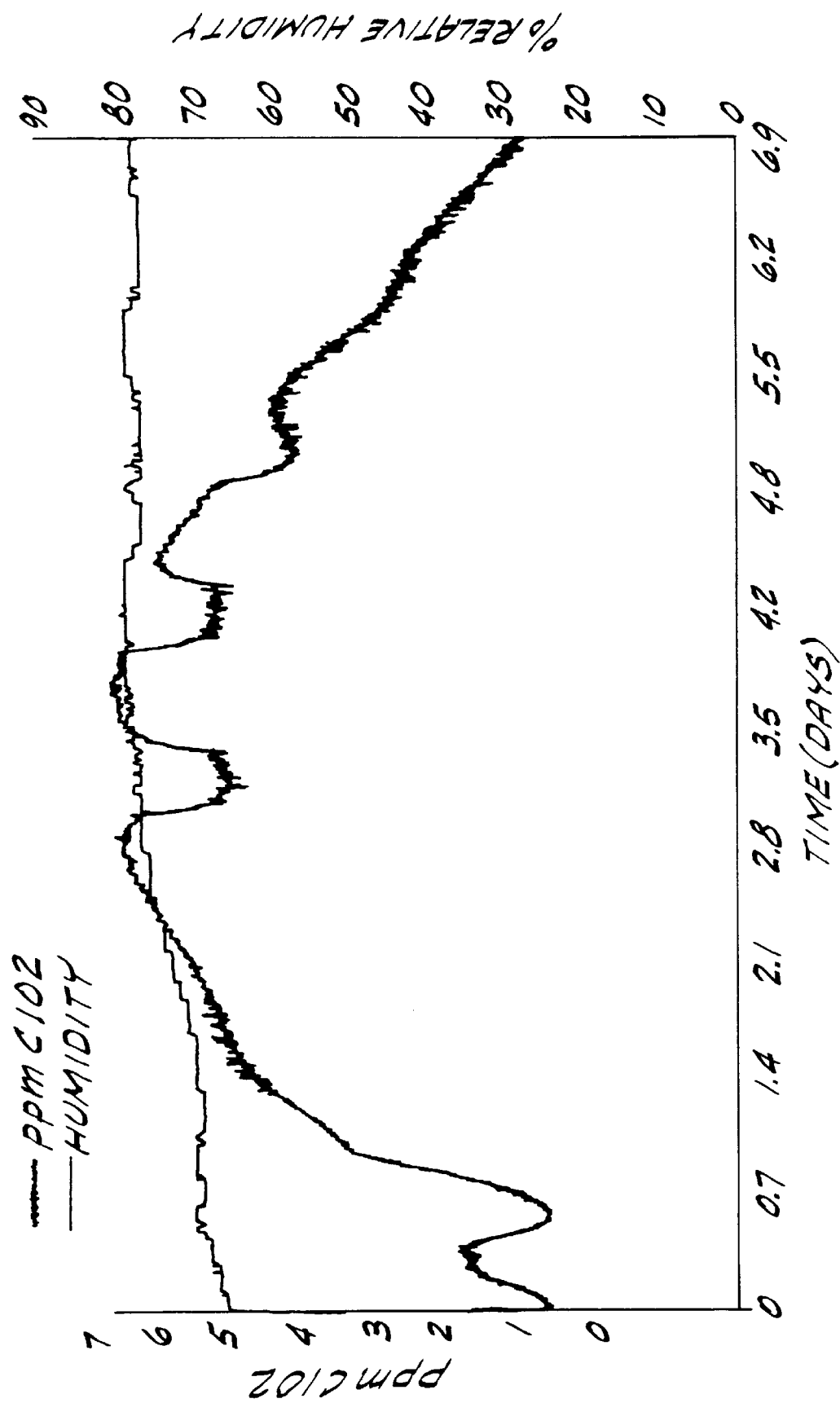
Figure 16:
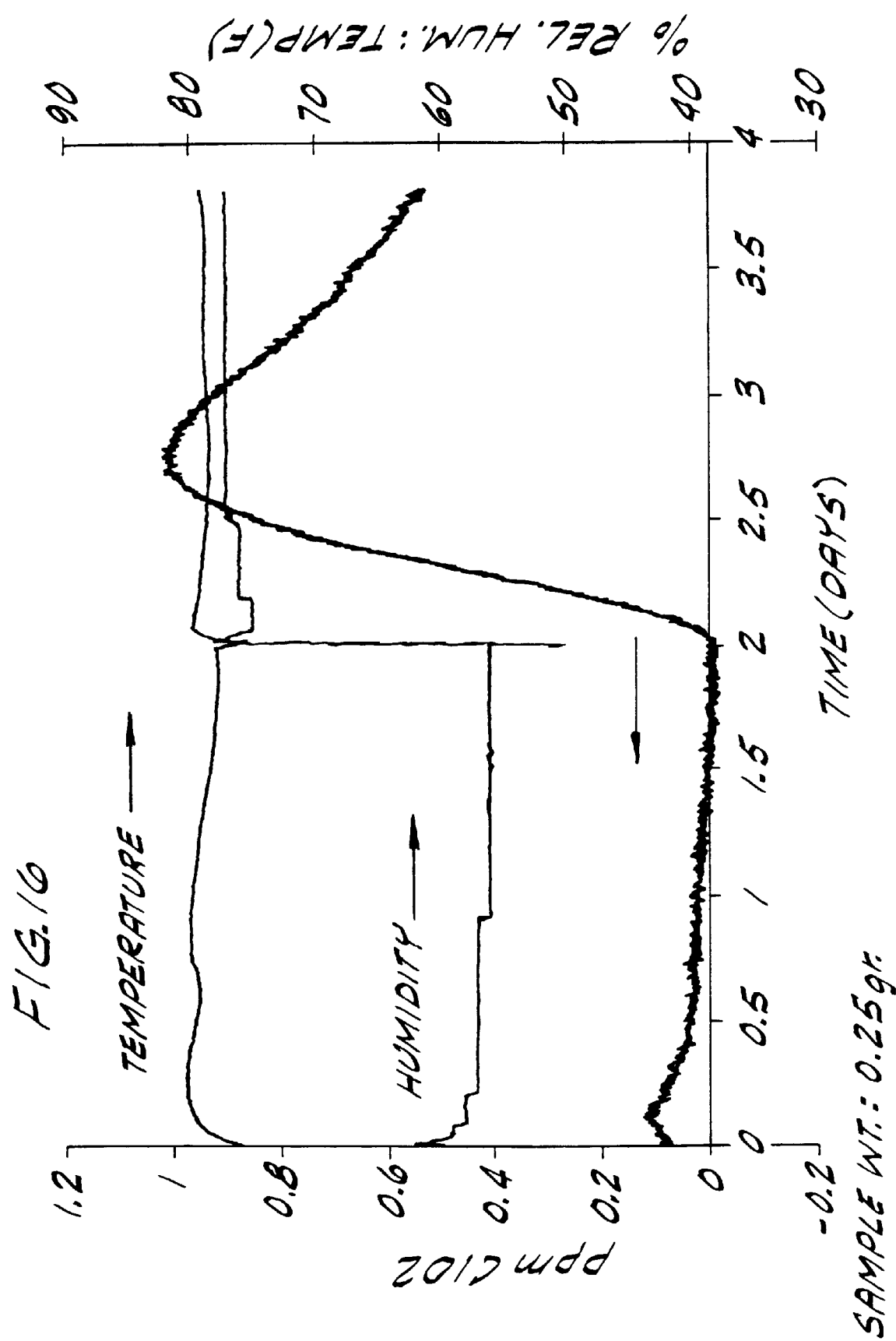
FIG. 16 is a plot of chlorine dioxide concentration, temperature and humidity as a function of time for a powder composition.

FIGS. 14 and 15 show the chlorine dioxide release rate from the powder. Minimal chlorine dioxide was released at about room temperature and about 10–14% relative humidity as shown in FIG. 14. FIG. 16 shows that significant release started as soon as the relative humidity exceeded about 60%. Controlled release for a week is shown at about room temperature and about 60–80% relative humidity in FIG. 15. Chlorine dioxide release rates are dependent on both temperature and relative humidity.

Figure 17:
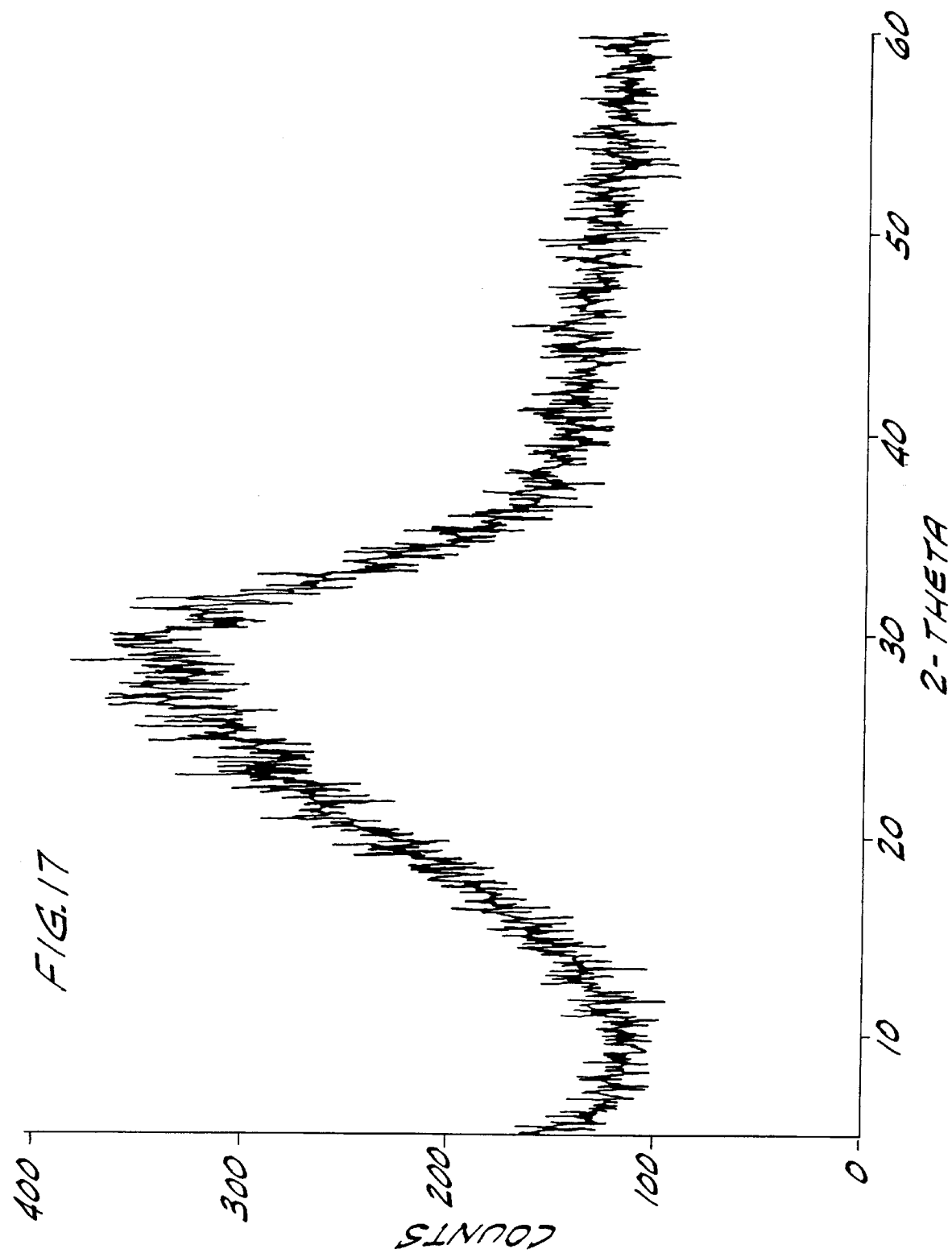
FIG. 17 is a plot of an x-ray diffraction pattern for a powder composition.

FIG. 17 shows the x-ray diffraction scattering pattern for the powder. The plot indicates that the powder is substantially amorphous.

EXAMPLE 4
One Step Powder Preparation Process 21.3 liters of a sodium silicate aqueous solution ($SiO_2$/$Na_2O$ ratio=3.22; 38.3% solids) was placed in a vessel equipped with a mechanical stirrer. 20 liters of a 10% sodium chlorite aqueous solution was added with vigorous stirring. A 50% sodium polyphosphate (($NaPO_3$)$_x$) aqueous solution was then added with vigorous stirring. The resulting solution was immediately spray dried in a commercial spray drying unit at the conditions described in Example 2. The product was usually somewhat moist (4–8% water) and was further dried immediately to below 1% water in a vacuum oven (100° C./30 in. Hg vacuum).

EXAMPLE 5
Percolation Network Preparation Process

The powder of Example 3 was milled (10 wt. %) and homogenized with 5 wt. % polyethylene glycol and 85 wt. % Astorwax 8357 microcrystalline wax (commercially available from Astor Wax Corp., Doraville, Ga.). The blended wax was melted at about 195° C. and coated onto Xerox® printer paper using a Waxmaster coater. The coated paper was then exposed to humidity. Release of chlorine dioxide after exposure to moisture was demonstrated using a chlorine test strip. After a few hours, no gas release was observed. However, the paper turned green after about 12 hours, indicating the slow release of chlorine dioxide from the coating.

EXAMPLE 6
Percolation Network Preparation Process

The powder of Example 3 was blended with sodium sulfate (1:1 volume ratio) and dried. The blend was mixed with melted Gulf paraffin wax or melted Astor 3040L microcrystalline wax in volume ratios of blend to wax of 1:3 and 1:4. The 1:3 material released chlorine dioxide after exposure to moisture as demonstrated using a chlorine test strip. The 1:4 material did not release chlorine dioxide, which indicated that a percolation network containing an inorganic salt as a humectant may require more than 10 wt. % of the humectant in the network to activate the gas-generating material.

U.S. Pat. Nos. 5,360,609, 5,631,300, 5,639,295, 5,650,446, 5,668,185, 5,695,814, 5,705,092, and 5,707,739, and U.S. patent application Ser. Nos. 08/016,904, 08/724,907, 08/858,859, 08/858,860, and 08/924,684 are incorporated herein by reference in their entirety.

While the invention is susceptible to various modifications and alternative forms, specific embodiments thereof have been shown by way of example in the drawings and have been described herein in detail. It should be understood, however, that it is not intended to limit the invention to the particular form disclosed, but on the contrary, the intention is to cover all modifications, equivalents and alternatives falling within the spirit and scope of the invention as defined by the appended claims.

We claim:

1. A composition comprising a hydrophobic phase and a hydrophilic phase containing a percolation agent and a gas-generating material, the composition being a co-continuous network or a discontinuous network which contains passages formed by the percolation agent, the passages being capable of transmitting moisture to the gas-generating material to generate and release a gas.

2. A composition comprising a hydrophobic phase and a hydrophilic phase containing a percolation agent and a powder, the composition being a co-continuous network or a discontinuous network which contains passages formed by the percolation agent, the passages being capable of transmitting moisture to the powder to generate and release a gas, wherein the powder comprises anions dissolved in an amorphous, paracrystalline or crystalline solid solution, the anions being capable of reacting with hydronium ions to generate a gas; and an acid releasing agent, the powder being substantially free of water and capable of generating and releasing a gas after hydrolysis of the acid releasing agent.

3. A composition comprising a hydrophobic phase and a hydrophilic phase containing a percolation agent and a powder, the composition being a co-continuous network or a discontinuous network which contains passages formed by the percolation agent, the passages being capable of transmitting moisture to the powder to generate and release a gas, wherein the powder comprises an interpenetrating network containing a silicate, anions that are capable of reacting with hydronium ions to generate a gas, and an acid releasing agent; the powder being substantially free of water and capable of generating and releasing a gas after hydrolysis of the acid releasing agent.

4. A composition comprising a hydrophobic phase and a hydrophilic phase containing a percolation agent and a powder, the composition being a co-continuous network or a discontinuous network which contains passages formed by the percolation agent, the passages being capable of transmitting moisture to the powder to generate and release a gas, wherein the powder comprises a core containing a silicate and anions that are capable of reacting with hydronium ions to generate a gas; a first layer containing an acid releasing agent; and a second layer between the core and the first layer, the second layer containing a silicate; the core and the first and second layers being substantially free of water, the second layer being substantially water-insoluble, and the core being capable of generating and releasing a gas after hydrolysis of the acid releasing agent.

5. A composition comprising a hydrophobic phase and a hydrophilic phase containing a percolation agent and a powder, the composition being a co-continuous network or a discontinuous network which contains passages formed by the percolation agent, the passages being capable of transmitting moisture to the powder to generate and release a gas, wherein the powder comprises a core containing a silicate and anions that are capable of reacting with hydronium ions to generate a gas; and a layer on the outer surface of the core, the layer containing an acid releasing agent and a silicate; the core and the layer being substantially free of water, the layer being substantially water-insoluble, and the core being capable of generating and releasing a gas after hydrolysis of the acid releasing agent.

* * * * *